US008748127B2

(12) United States Patent
Li et al.

(10) Patent No.: US 8,748,127 B2
(45) Date of Patent: *Jun. 10, 2014

(54) TRUNCATED L1 PROTEIN OF HUMAN PAPILLOMAVIRUS TYPE 6

(75) Inventors: Shaowei Li, Xiamen (CN); Huirong Pan, Xiamen (CN); Bo Liu, Xiamen (CN); Jun Zhang, Xiamen (CN); Ji Miao, Xiamen (CN); Ningshao Xia, Xiamen (CN)

(73) Assignees: Xiamen University, Xiamen, Fujian Province (CN); Beijing Wantai Biological Pharmacy Enterprise Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/601,972

(22) PCT Filed: May 29, 2008

(86) PCT No.: PCT/CN2008/001050
§ 371 (c)(1),
(2), (4) Date: Dec. 30, 2009

(87) PCT Pub. No.: WO2008/145021
PCT Pub. Date: Dec. 4, 2008

(65) Prior Publication Data
US 2010/0255021 A1  Oct. 7, 2010

(30) Foreign Application Priority Data

May 29, 2007  (CN) .......................... 2007 1 0105764

(51) Int. Cl.
*A61K 39/12* (2006.01)
*C07K 14/05* (2006.01)
*C12N 7/00* (2006.01)
*C07K 14/005* (2006.01)
*C07K 14/025* (2006.01)

(52) U.S. Cl.
CPC ............ *C07K 14/005* (2013.01); *C07K 14/025* (2013.01); *G01N 2333/025* (2013.01); *C12N 2710/00* (2013.01); *C12N 2700/00* (2013.01)
USPC ................... 435/69.1; 424/186.1; 424/204.1; 424/202.1; 435/252.8; 435/320.1; 530/350; 536/23.72

(58) Field of Classification Search
None
See application file for complete search history.

(56) References Cited

U.S. PATENT DOCUMENTS

| | | | |
|---|---|---|---|
| 5,866,553 A * | 2/1999 | Donnelly et al. | 514/44 R |
| 6,013,262 A * | 1/2000 | Frazer et al. | 424/204.1 |
| 6,599,508 B1 * | 7/2003 | Gissmann et al. | 424/204.1 |
| 7,351,533 B2 * | 4/2008 | McCarthy et al. | 435/6.14 |
| 7,709,010 B2 * | 5/2010 | Bryan et al. | 424/278.1 |
| 7,754,430 B2 * | 7/2010 | Gissmann et al. | 435/5 |
| 2002/0193565 A1 * | 12/2002 | Stanley et al. | 530/350 |
| 2003/0118609 A1 * | 6/2003 | Harrison et al. | 424/204.1 |
| 2004/0081661 A1 | 4/2004 | Hallek et al. | |
| 2005/0031636 A1 * | 2/2005 | Gissman et al. | 424/186.1 |
| 2005/0175632 A1 * | 8/2005 | Wettendorff | 424/204.1 |
| 2006/0153864 A1 * | 7/2006 | Gissmann et al. | 424/186.1 |
| 2006/0198853 A1 * | 9/2006 | Gissmann et al. | 424/204.1 |
| 2007/0224218 A1 * | 9/2007 | Wettendorff | 424/204.1 |
| 2008/0248062 A1 * | 10/2008 | Bryan et al. | 424/204.1 |
| 2008/0279890 A1 * | 11/2008 | Wettendorff | 424/204.1 |
| 2009/0028894 A1 * | 1/2009 | Gissmann et al. | 424/192.1 |
| 2010/0255031 A1 * | 10/2010 | Gu et al. | 424/204.1 |
| 2010/0272751 A1 * | 10/2010 | Li et al. | 424/204.1 |
| 2010/0291141 A1 * | 11/2010 | Zhang et al. | 424/204.1 |

FOREIGN PATENT DOCUMENTS

| | | | |
|---|---|---|---|
| CN | 1478790 | | 3/2004 |
| CN | 1478790 A | * | 3/2004 |
| CN | 101153280 | | 4/2008 |
| EP | 2 147 926 | | 1/2010 |
| WO | WO 94/20137 | | 9/1994 |
| WO | WO 00/54730 | | 9/2000 |
| WO | WO 03/078455 | | 9/2003 |

OTHER PUBLICATIONS

Written Opinion of the International Searching Authority for PCT/CN2008/001050. English version. Dated Sep. 11, 2008.*
Machine translation (Chinese to English) of CN1478790A. Mar. 2004.*
Dartmann K, Schwarz E, Gissmann L, zur Hausen H. The nucleotide sequence and genome organization of human papilloma virus type 11. Virology. May 1986;151(1):124-30.*
Chen XS, Casini G, Harrison SC, Garcea RL. Papillomavirus capsid protein expression in *Escherichia coli*: purification and assembly of HPV11 and HPV16 L1. J Mol Biol. Mar. 16, 2001;307(1):173-82.*
Schiller JT, Castellsagué X, Garland SM. A review of clinical trials of human papillomavirus prophylactic vaccines. Vaccine. Nov. 20, 2012;30 Suppl 5:F123-38.*
Cho HJ, Oh YK, Kim YB. Advances in human papilloma virus vaccines: a patent review. Expert Opin Ther Pat. Mar. 2011;21(3):295-309. Epub Jan. 21, 2011.*
Neeper et. al. HPV6 protein coding sequence. NCBI-GenBank. Acc. # AAC53712; submitted Apr. 19, 1996.*
Bishop B, et. al. Virol J. Jan. 8, 2007;4:3.*
European Search Report dated Mar. 9, 2011.
Kelsall et al., "Expression of the Major Capsid Protein of Human Papillomarvirus Type 16 in *Escherichia Coli*"; Journal of Virological Methods, Elsevier, BV, NL, vol. 53, No. 1, Jan. 1, 1995.
International Search Report, May 29, 2007.
Wang, Jiabi et al., "Expression of Recombinant HPV6 L1 Protein in Prokaryotic System"; Journal Clinical Dermatol, Jun. 2003, vol. 32, No. 6, ISSN 1000-4963.
W. Caparros-Wanderley et al.; "Intratype Sequence Variation Among Clinical Isolates of the Human Papillomavirus Type 6 L1 ORF: Clustering of Mutations and Identification of a Frequent Amino Acid Sequence Variant"; Journal of General Virology, Apr. 1999; vol. 80, pp. 1025-1033, ISSN 0001-5983.
European Search Report dated Jan. 27, 2014.

* cited by examiner

*Primary Examiner* — Benjamin P Blumel
*Assistant Examiner* — Rachel Gill
(74) *Attorney, Agent, or Firm* — Pillsbury Winthrop Shaw Pittman, LLP

(57) ABSTRACT

The invention relates to a truncated L1 protein of the Human Papillomavirus Type 6, a virus-like particle consisting of the protein, a vaccine comprising said virus-like particle, and the use of the vaccine in the prevention of condyloma acuminatum or HPV infections.

14 Claims, 7 Drawing Sheets

FIG. 10
1
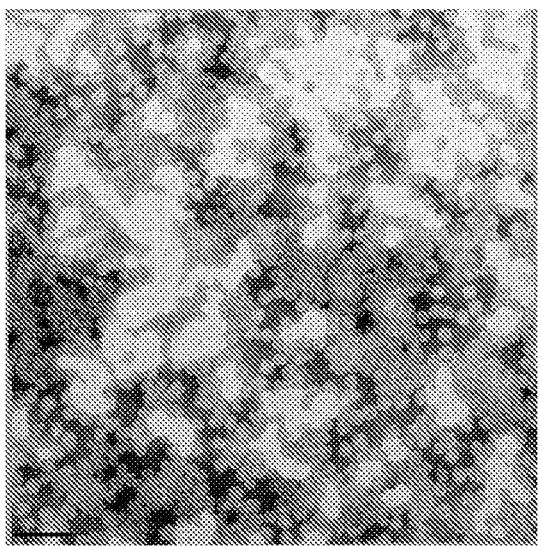
2
3
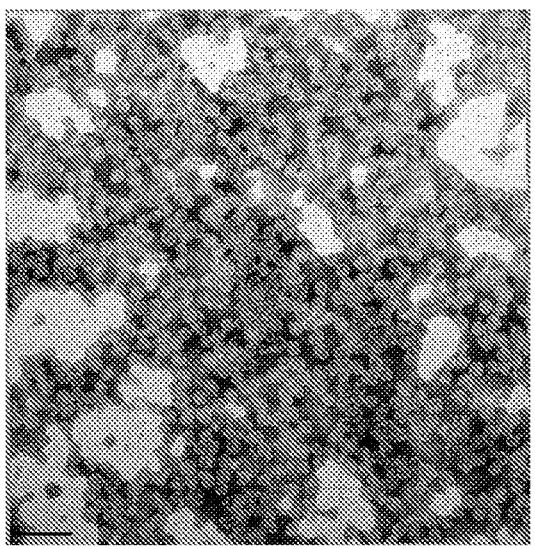

SEQUENCE LISTING

```
<160> NUMBER OF SEQ ID NOS: 11

<210> SEQ ID NO 1
<211> LENGTH: 498
<212> TYPE: PRT
<213> ORGANISM: Artifical
<220> FEATURE:
<223> OTHER INFORMATION: HPV

<400> SEQUENCE: 1

Met Pro Ser Asp Ser Thr Val Tyr Val Pro Pro Asn Pro Val Ser
1               5                   10                  15

Lys Val Val Ala Thr Asp Ala Tyr Val Thr Arg Thr Asn Ile Phe Tyr
            20                  25                  30

His Ala Ser Ser Ser Arg Leu Leu Ala Val Gly His Pro Tyr Phe Ser
        35                  40                  45

Ile Lys Arg Ala Asn Lys Thr Val Val Pro Lys Val Ser Gly Tyr Gln
    50                  55                  60

Tyr Arg Val Phe Lys Val Val Leu Pro Asp Pro Asn Lys Phe Ala Leu
```

-continued

|     |     |     |     |     |     |     |     |     |     |     |     |
| --- | --- | --- | --- | --- | --- | --- | --- | --- | --- | --- | --- |
| 65  |     |     |     | 70  |     |     |     | 75  |     |     | 80  |
| Pro | Asp | Ser | Ser | Leu | Phe | Asp | Pro | Thr | Thr | Gln | Arg | Leu | Val | Trp | Ala |

Pro Asp Ser Ser Leu Phe Asp Pro Thr Thr Gln Arg Leu Val Trp Ala
 65                  70                  75                  80

Cys Thr Gly Leu Glu Val Gly Arg Gly Gln Pro Leu Gly Val Gly Val
                 85                  90                  95

Ser Gly His Pro Phe Leu Asn Lys Tyr Asp Asp Val Glu Asn Ser Gly
            100                 105                 110

Ser Gly Gly Asn Pro Gly Gln Asp Asn Arg Val Asn Val Gly Met Asp
        115                 120                 125

Tyr Lys Gln Thr Gln Leu Cys Met Val Gly Cys Ala Pro Pro Leu Gly
130                 135                 140

Glu His Trp Gly Lys Gly Lys Gln Cys Thr Asn Thr Pro Val Gln Ala
145                 150                 155                 160

Gly Asp Cys Pro Pro Leu Glu Leu Ile Thr Ser Val Ile Gln Asp Gly
                165                 170                 175

Asp Met Val Asp Thr Gly Phe Gly Ala Met Asn Phe Ala Asp Leu Gln
            180                 185                 190

Thr Asn Lys Ser Asp Val Pro Ile Asp Ile Cys Gly Thr Thr Cys Lys
        195                 200                 205

Tyr Pro Asp Tyr Leu Gln Met Ala Ala Asp Pro Tyr Gly Asp Arg Leu
210                 215                 220

Phe Phe Phe Leu Arg Lys Glu Gln Met Phe Ala Arg His Phe Phe Asn
225                 230                 235                 240

Arg Ala Gly Glu Val Gly Glu Pro Val Pro Asp Thr Leu Ile Ile Lys
                245                 250                 255

Gly Ser Gly Asn Arg Thr Ser Val Gly Ser Ser Ile Tyr Val Asn Thr
            260                 265                 270

Pro Ser Gly Ser Leu Val Ser Ser Glu Ala Gln Leu Phe Asn Lys Pro
        275                 280                 285

Tyr Trp Leu Gln Lys Ala Gln Gly His Asn Asn Gly Ile Cys Trp Gly
290                 295                 300

Asn Gln Leu Phe Val Thr Val Val Asp Thr Thr Arg Ser Thr Asn Met
305                 310                 315                 320

Thr Leu Cys Ala Ser Val Thr Thr Ser Ser Thr Tyr Thr Asn Ser Asp
                325                 330                 335

Tyr Lys Glu Tyr Met Arg His Val Glu Glu Tyr Asp Leu Gln Phe Ile
            340                 345                 350

Phe Gln Leu Cys Ser Ile Thr Leu Ser Ala Glu Val Val Ala Tyr Ile
        355                 360                 365

His Thr Met Asn Pro Ser Val Leu Glu Asp Trp Asn Phe Gly Leu Ser
370                 375                 380

Pro Pro Pro Asn Gly Thr Leu Glu Asp Thr Tyr Arg Tyr Val Gln Ser
385                 390                 395                 400

Gln Ala Ile Thr Cys Gln Lys Pro Thr Pro Glu Lys Gln Lys Pro Asp
                405                 410                 415

Pro Tyr Lys Asn Leu Ser Phe Trp Glu Val Asn Leu Lys Glu Lys Phe
            420                 425                 430

Ser Ser Glu Leu Asp Gln Tyr Pro Leu Gly Arg Lys Phe Leu Leu Gln
        435                 440                 445

Ser Gly Tyr Arg Gly Arg Ser Ser Ile Arg Thr Gly Val Lys Arg Pro
450                 455                 460

Ala Val Ser Lys Ala Ser Ala Ala Pro Lys Arg Lys Arg Ala Lys Thr
465                 470                 475                 480

Lys Arg

<210> SEQ ID NO 2
<211> LENGTH: 499
<212> TYPE: PRT
<213> ORGANISM: Artifical
<220> FEATURE:
<223> OTHER INFORMATION: HPV

<400> SEQUENCE: 2

```
Met Arg Pro Ser Asp Ser Thr Val Tyr Val Pro Pro Asn Pro Val
1               5                   10                  15

Ser Lys Val Val Ala Thr Asp Ala Tyr Val Thr Arg Thr Asn Ile Phe
                20                  25                  30

Tyr His Ala Ser Ser Ser Arg Leu Leu Ala Val Gly His Pro Tyr Phe
                35                  40                  45

Ser Ile Lys Arg Ala Asn Lys Thr Val Pro Lys Val Ser Gly Tyr
                50              55                  60

Gln Tyr Arg Val Phe Lys Val Val Leu Pro Asp Pro Asn Lys Phe Ala
65                  70                  75                  80

Leu Pro Asp Ser Ser Leu Phe Asp Pro Thr Thr Gln Arg Leu Val Trp
                    85                  90                  95

Ala Cys Thr Gly Leu Glu Val Gly Arg Gly Gln Pro Leu Gly Val Gly
                100                 105                 110

Val Ser Gly His Pro Phe Leu Asn Lys Tyr Asp Asp Val Glu Asn Ser
                115                 120                 125

Gly Ser Gly Gly Asn Pro Gly Gln Asp Asn Arg Val Asn Val Gly Met
130                 135                 140

Asp Tyr Lys Gln Thr Gln Leu Cys Met Val Gly Cys Ala Pro Pro Leu
145                 150                 155                 160

Gly Glu His Trp Gly Lys Gly Lys Gln Cys Thr Asn Thr Pro Val Gln
                165                 170                 175

Ala Gly Asp Cys Pro Pro Leu Glu Leu Ile Thr Ser Val Ile Gln Asp
                180                 185                 190

Gly Asp Met Val Asp Thr Gly Phe Gly Ala Met Asn Phe Ala Asp Leu
                195                 200                 205

Gln Thr Asn Lys Ser Asp Val Pro Ile Asp Ile Cys Gly Thr Thr Cys
210                 215                 220

Lys Tyr Pro Asp Tyr Leu Gln Met Ala Ala Asp Pro Tyr Gly Asp Arg
225                 230                 235                 240

Leu Phe Phe Phe Leu Arg Lys Glu Gln Met Phe Ala Arg His Phe Phe
                245                 250                 255

Asn Arg Ala Gly Glu Val Gly Glu Pro Val Pro Asp Thr Leu Ile Ile
                260                 265                 270

Lys Gly Ser Gly Asn Arg Thr Ser Val Gly Ser Ser Ile Tyr Val Asn
                275                 280                 285

Thr Pro Ser Gly Ser Leu Val Ser Ser Glu Ala Gln Leu Phe Asn Lys
                290                 295                 300

Pro Tyr Trp Leu Gln Lys Ala Gln Gly His Asn Asn Gly Ile Cys Trp
305                 310                 315                 320

Gly Asn Gln Leu Phe Val Thr Val Val Asp Thr Thr Arg Ser Thr Asn
                325                 330                 335

Met Thr Leu Cys Ala Ser Val Thr Thr Ser Ser Thr Tyr Thr Asn Ser
                340                 345                 350

Asp Tyr Lys Glu Tyr Met Arg His Val Glu Glu Tyr Asp Leu Gln Phe
                355                 360                 365
```

```
Ile Phe Gln Leu Cys Ser Ile Thr Leu Ser Ala Glu Val Val Ala Tyr
    370                 375                 380
Ile His Thr Met Asn Pro Ser Val Leu Glu Asp Trp Asn Phe Gly Leu
385                 390                 395                 400
Ser Pro Pro Pro Asn Gly Thr Leu Glu Asp Thr Tyr Arg Tyr Val Gln
                405                 410                 415
Ser Gln Ala Ile Thr Cys Gln Lys Pro Thr Pro Glu Lys Gln Lys Pro
            420                 425                 430
Asp Pro Tyr Lys Asn Leu Ser Phe Trp Glu Val Asn Leu Lys Glu Lys
        435                 440                 445
Phe Ser Ser Glu Leu Asp Gln Tyr Pro Leu Gly Arg Lys Phe Leu Leu
    450                 455                 460
Gln Ser Gly Tyr Arg Gly Arg Ser Ser Ile Arg Thr Gly Val Lys Arg
465                 470                 475                 480
Pro Ala Val Ser Lys Ala Ser Ala Ala Pro Lys Arg Lys Arg Ala Lys
                485                 490                 495
Thr Lys Arg

<210> SEQ ID NO 3
<211> LENGTH: 497
<212> TYPE: PRT
<213> ORGANISM: Artifical
<220> FEATURE:
<223> OTHER INFORMATION: HPV

<400> SEQUENCE: 3

Met Ser Asp Ser Thr Val Tyr Val Pro Pro Asn Pro Val Ser Lys
1               5                   10                  15
Val Val Ala Thr Asp Ala Tyr Val Thr Arg Thr Asn Ile Phe Tyr His
                20                  25                  30
Ala Ser Ser Ser Arg Leu Leu Ala Val Gly His Pro Tyr Phe Ser Ile
            35                  40                  45
Lys Arg Ala Asn Lys Thr Val Val Pro Lys Val Ser Gly Tyr Gln Tyr
        50                  55                  60
Arg Val Phe Lys Val Val Leu Pro Asp Pro Asn Lys Phe Ala Leu Pro
65                  70                  75                  80
Asp Ser Ser Leu Phe Asp Pro Thr Thr Gln Arg Leu Val Trp Ala Cys
                85                  90                  95
Thr Gly Leu Glu Val Gly Arg Gly Gln Pro Leu Gly Val Gly Val Ser
            100                 105                 110
Gly His Pro Phe Leu Asn Lys Tyr Asp Asp Val Glu Asn Ser Gly Ser
        115                 120                 125
Gly Gly Asn Pro Gly Gln Asp Asn Arg Val Asn Val Gly Met Asp Tyr
    130                 135                 140
Lys Gln Thr Gln Leu Cys Met Val Gly Cys Ala Pro Pro Leu Gly Glu
145                 150                 155                 160
His Trp Gly Lys Gly Lys Gln Cys Thr Asn Thr Pro Val Gln Ala Gly
                165                 170                 175
Asp Cys Pro Pro Leu Glu Leu Ile Thr Ser Val Ile Gln Asp Gly Asp
            180                 185                 190
Met Val Asp Thr Gly Phe Gly Ala Met Asn Phe Ala Asp Leu Gln Thr
        195                 200                 205
Asn Lys Ser Asp Val Pro Ile Asp Ile Cys Gly Thr Thr Cys Lys Tyr
    210                 215                 220
Pro Asp Tyr Leu Gln Met Ala Ala Asp Pro Tyr Gly Asp Arg Leu Phe
```

```
                225                 230                 235                 240
Phe Phe Leu Arg Lys Glu Gln Met Phe Ala Arg His Phe Phe Asn Arg
                245                 250                 255
Ala Gly Glu Val Gly Glu Pro Val Pro Asp Thr Leu Ile Ile Lys Gly
                260                 265                 270
Ser Gly Asn Arg Thr Ser Val Gly Ser Ser Ile Tyr Val Asn Thr Pro
                275                 280                 285
Ser Gly Ser Leu Val Ser Ser Glu Ala Gln Leu Phe Asn Lys Pro Tyr
                290                 295                 300
Trp Leu Gln Lys Ala Gln Gly His Asn Asn Gly Ile Cys Trp Gly Asn
305                 310                 315                 320
Gln Leu Phe Val Thr Val Val Asp Thr Thr Arg Ser Thr Asn Met Thr
                325                 330                 335
Leu Cys Ala Ser Val Thr Thr Ser Ser Thr Tyr Thr Asn Ser Asp Tyr
                340                 345                 350
Lys Glu Tyr Met Arg His Val Glu Glu Tyr Asp Leu Gln Phe Ile Phe
                355                 360                 365
Gln Leu Cys Ser Ile Thr Leu Ser Ala Glu Val Val Ala Tyr Ile His
                370                 375                 380
Thr Met Asn Pro Ser Val Leu Glu Asp Trp Asn Phe Gly Leu Ser Pro
385                 390                 395                 400
Pro Pro Asn Gly Thr Leu Glu Asp Thr Tyr Arg Tyr Val Gln Ser Gln
                405                 410                 415
Ala Ile Thr Cys Gln Lys Pro Thr Pro Glu Lys Gln Lys Pro Asp Pro
                420                 425                 430
Tyr Lys Asn Leu Ser Phe Trp Glu Val Asn Leu Lys Glu Lys Phe Ser
                435                 440                 445
Ser Glu Leu Asp Gln Tyr Pro Leu Gly Arg Lys Phe Leu Leu Gln Ser
                450                 455                 460
Gly Tyr Arg Gly Arg Ser Ser Ile Arg Thr Gly Val Lys Arg Pro Ala
465                 470                 475                 480
Val Ser Lys Ala Ser Ala Ala Pro Lys Arg Lys Arg Ala Lys Thr Lys
                485                 490                 495
Arg

<210> SEQ ID NO 4
<211> LENGTH: 496
<212> TYPE: PRT
<213> ORGANISM: Artifical
<220> FEATURE:
<223> OTHER INFORMATION: HPV

<400> SEQUENCE: 4

Met Asp Ser Thr Val Tyr Val Pro Pro Asn Pro Val Ser Lys Val
1               5                   10                  15
Val Ala Thr Asp Ala Tyr Val Thr Arg Thr Asn Ile Phe Tyr His Ala
                20                  25                  30
Ser Ser Ser Arg Leu Leu Ala Val Gly His Pro Tyr Phe Ser Ile Lys
                35                  40                  45
Arg Ala Asn Lys Thr Val Val Pro Lys Val Ser Gly Tyr Gln Tyr Arg
                50                  55                  60
Val Phe Lys Val Val Leu Pro Asp Pro Asn Lys Phe Ala Leu Pro Asp
65                  70                  75                  80
Ser Ser Leu Phe Asp Pro Thr Thr Gln Arg Leu Val Trp Ala Cys Thr
                85                  90                  95
```

```
Gly Leu Glu Val Gly Arg Gly Gln Pro Leu Gly Val Gly Val Ser Gly
                100                 105                 110

His Pro Phe Leu Asn Lys Tyr Asp Asp Val Glu Asn Ser Gly Ser Gly
            115                 120                 125

Gly Asn Pro Gly Gln Asp Asn Arg Val Asn Val Gly Met Asp Tyr Lys
130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
            195                 200                 205

Lys Ser Asp Val Pro Ile Asp Ile Cys Gly Thr Thr Cys Lys Tyr Pro
210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
            275                 280                 285

Gly Ser Leu Val Ser Ser Glu Ala Gln Leu Phe Asn Lys Pro Tyr Trp
            290                 295                 300

Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
            340                 345                 350

Glu Tyr Met Arg His Val Glu Glu Tyr Asp Leu Gln Phe Ile Phe Gln
            355                 360                 365

Leu Cys Ser Ile Thr Leu Ser Ala Glu Val Val Ala Tyr Ile His Thr
370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
            435                 440                 445

Glu Leu Asp Gln Tyr Pro Leu Gly Arg Lys Phe Leu Leu Gln Ser Gly
            450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495

<210> SEQ ID NO 5
<211> LENGTH: 1503
<212> TYPE: DNA
<213> ORGANISM: Artifical
```

<220> FEATURE:
<223> OTHER INFORMATION: HPV

<400> SEQUENCE: 5

```
atgtggcggc ctagcgacag cacagtatat gtgcctcctc ctaaccctgt atccaaagtt      60
gttgccacgg atgcttatgt tactcgcacc aacatatttt atcatgccag cagttctaga     120
cttcttgcag tgggtcatcc ttattttttcc ataaaacggg ctaacaaaac tgttgtgcca     180
aaggtgtcag gatatcaata cagggtattt aaggtggtgt taccagatcc taacaaattt     240
gcattgcctg actcgtctct ttttgatccc acaacacaac gtttggtatg ggcatgcaca     300
ggcctagagg tgggcagggg acagccatta ggtgtgggtg taagtggaca ccttttccta     360
aataaatatg atgatgttga aaattcaggg agtggtggta accctggaca ggataacagg     420
gttaatgttg gtatggatta taaacaaaca caattatgca tggttggatg tgccccccct     480
ttgggcgagc attggggtaa aggtaaacag tgtactaata cacctgtaca ggctggtgac     540
tgcccgccct tagaacttat taccagtgtt atacaggatg gcgatatggt tgacacaggc     600
tttggtgcta tgaattttgc tgatttgcag accaataaat cagatgttcc tattgacata     660
tgtggcacta catgtaaaata tccagattat ttacaaatgg ctgcagaccc atatggtgat     720
agattatttt tttttctacg gaaggaacaa atgtttgcca gcatttttt taacagggct     780
ggcgaggtgg gggaacctgt gcctgatact cttataatta agggtagtgg aaatcgaacg     840
tctgtaggga gtagtatata tgttaacacc ccaagcggct cttggtgtc ctctgaggca     900
caattgttta ataagccata ttggctacaa aaagcccagg acataacaa tggtatttgt     960
tggggtaatc aactgtttgt tactgtggta gataccacac gcagtaccaa catgacatta    1020
tgtgcatccg taactacatc ttccacatac accaattctg attataaaga gtacatgcgt    1080
catgtggaag agtatgattt acaatttatt tttcaattat gtagcattac attgtctgct    1140
gaagtaatgg cctatattca cacaatgaat ccctctgttt tggaagactg gaactttggg    1200
ttatcgcctc ccccaaatgg tacattagaa gatacctata ggtatgtgca gtcacaggcc    1260
attacctgtc aaaagcccac tcctgaaaag caaaagccag atccctataa gaaccttagt    1320
ttttgggagg ttaatttaaa agaaaagttt tctagtgaat tggatcagta tcctttggga    1380
cgcaagtttt tgttacaaag tggatatagg ggacggtcct ctattcgtac cggtgttaag    1440
cgccctgctg tttccaaagc ctctgctgcc cctaaacgta agcgcgccaa aactaaaagg    1500
taa                                                                  1503
```

<210> SEQ ID NO 6
<211> LENGTH: 1497
<212> TYPE: DNA
<213> ORGANISM: Artifical
<220> FEATURE:
<223> OTHER INFORMATION: HPV

<400> SEQUENCE: 6

```
atgcctagcg acagcacagt atatgtgcct cctcctaacc ctgtatccaa agttgttgcc      60
acggatgctt atgttactcg caccaacata ttttatcatg ccagcagttc tagacttctt     120
gcagtgggtc atccttattt ttccataaaa cgggctaaca aaactgttgt gccaaaggtg     180
tcaggatatc aatacagggt atttaaggtg gtgttaccag atcctaacaa atttgcattg     240
cctgactcgt ctcttttga tcccacaaca caacgtttgg tatgggcatg cacaggccta     300
gaggtgggca ggggacagcc attaggtgtg ggtgtaagtg gacatccttt tctaaataaa     360
tatgatgatg ttgaaaattc agggagtggt ggtaaccctg gacaggataa cagggttaat     420
```

```
gttggtatgg attataaaca aacacaatta tgcatggttg gatgtgcccc ccctttgggc      480
gagcattggg gtaaaggtaa acagtgtact aatacacctg tacaggctgg tgactgcccg      540
cccttagaac ttattaccag tgttatacag gatggcgata tggttgacac aggctttggt      600
gctatgaatt ttgctgattt gcagaccaat aaatcagatg ttcctattga tatatgtggc      660
actacatgta aatatccaga ttatttacaa atggctgcag acccttatgg tgatagatta      720 ttttttttc tacggaagga acaaatgttt gccagacatt ttttaacag gctggcgag        780 gtggggggaac ctgtgcctga tactcttata attaaggta gtggaaatcg aacgtctgta      840
gggagtagta tatatgttaa caccccaagc ggctctttgg tgtcctctga ggcacaattg      900
tttaataagc catattggct acaaaaagcc cagggacata caatggtat ttgttggggt      960 aatcaactgt ttgttactgt ggtagatacc acacgcagta ccaacatgac attatgtgca     1020
tccgtaacta catcttccac atacaccaat tctgattata agagtacat gcgtcatgtg      1080 gaagagtatg atttacaatt tatttttcaa ttatgtagca ttcattgtc tgctgaagta      1140 gtggcctata ttcacacaat gaatccctct gttttggaag actggaactt tgggttatcg     1200
cctcccccaa atggtacatt agaagatacc tataggtatg tgcagtcaca ggccattacc     1260
tgtcaaaagc ccactcctga aaagcaaaag ccagatccct ataagaacct tagttttgg      1320 gaggttaatt taaagaaaaa gttttctagt gaattggatc agtatccttt gggacgcaag     1380
tttttgttac aaagtggata taggggacgg tcctctattc gtaccggtgt taagcgccct     1440
gctgtttcca agcctctgc tgccctaaa cgtaagcgcg ccaaaactaa aggtaa          1497

<210> SEQ ID NO 7
<211> LENGTH: 498
<212> TYPE: PRT
<213> ORGANISM: Artifical sequence
<220> FEATURE:
<223> OTHER INFORMATION: HPV

<400> SEQUENCE: 7

Met Ser Asp Ser Thr Val Tyr Val Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175
```

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
            195                 200                 205

Thr Asn Lys Ser Asp Val Pro Leu Asp Ile Cys Gly Thr Val Cys Lys
210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
            245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
            275                 280                 285

Pro Ser Gly Ser Leu Val Ser Ser Glu Ala Gln Leu Phe Asn Lys Pro
            290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
            325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
            355                 360                 365

Phe Gln Leu Cys Ser Ile Thr Leu Ser Ala Glu Val Met Ala Tyr Ile
370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
            405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
            435                 440                 445

Ser Ser Glu Leu Asp Gln Phe Pro Leu Gly Arg Lys Phe Leu Leu Gln
450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
            485                 490                 495

Lys Lys

<210> SEQ ID NO 8
<211> LENGTH: 502
<212> TYPE: PRT
<213> ORGANISM: Artifical sequence
<220> FEATURE:
<223> OTHER INFORMATION: HPV

<400> SEQUENCE: 8

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Phe Pro
            35                  40                  45

```
Ile Lys Lys Pro Asn Asn Lys Ile Leu Val Pro Lys Val Ser Gly
 50                  55                  60

Leu Gln Tyr Arg Val Phe Arg Ile His Leu Pro Asp Pro Asn Lys Phe
 65                  70                  75                  80

Gly Phe Pro Asp Thr Ser Phe Tyr Asn Pro Asp Thr Gln Arg Leu Val
                 85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285

Phe Pro Thr Pro Ser Gly Ser Met Val Thr Ser Asp Ala Gln Ile Phe
290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
370                 375                 380

Met Thr Tyr Ile His Ser Met Asn Ser Thr Ile Leu Glu Asp Trp Asn
385                 390                 395                 400

Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
450                 455                 460

Phe Leu Leu Gln Ala Gly Leu Glu Ala Lys Pro Lys Phe Thr Leu Gly
```

```
                465                 470                 475                 480
Lys Arg Lys Ala Thr Pro Thr Thr Ser Ser Thr Ser Thr Thr Ala Lys
                    485                 490                 495

Arg Lys Lys Arg Lys Leu
                500

<210> SEQ ID NO 9
<211> LENGTH: 504
<212> TYPE: PRT
<213> ORGANISM: Artifical sequence
<220> FEATURE:
<223> OTHER INFORMATION: HPV

<400> SEQUENCE: 9

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Asn Lys Gln Asp Ile Pro Lys Val Ser Ala
50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
            130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
            275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335
```

```
Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
            370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
            450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500

<210> SEQ ID NO 10
<211> LENGTH: 26
<212> TYPE: DNA
<213> ORGANISM: Artifical sequence
<220> FEATURE:
<223> OTHER INFORMATION: synthetic

<400> SEQUENCE: 10
catatgccta gcgacagcac agtata                                              26

<210> SEQ ID NO 11
<211> LENGTH: 26
<212> TYPE: DNA
<213> ORGANISM: Artifical sequence
<220> FEATURE:
<223> OTHER INFORMATION: synthetic

<400> SEQUENCE: 11
gtcgacttac cttttagttt tggcgc                                              26
```

US 8,748,127 B2

TRUNCATED L1 PROTEIN OF HUMAN PAPILLOMAVIRUS TYPE 6

CROSS REFERENCE TO RELATED APPLICATIONS

This is the U.S. National Phase of PCT/CN2008/001050, filed May 29, 2008, which in turn claims priority to Chinese Patent Application No. 200710105764.7, filed May 29, 2007, the contents of both of which are incorporated herein in their entirety by reference.

FIELD OF THE INVENTION

The invention relates to a truncated L1 protein of the Human Papillomavirus Type 6, a virus-like particle consisting of the protein, a vaccine comprising said virus-like particle, and the use of the vaccine in the prevention of condyloma acuminatum and HPV (especially HPV6) infection.

BACKGROUND OF THE INVENTION

The human papillomavirus, a non-enveloped, deoxyribonucleic acid (DNA) virus, belongs to the genus of papovaviridae. The viral genome is a closed circle, double-stranded DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. Viral particles are 45-55 nm in diameter, wherein the nucleocapsid, consisting of L1 and L2, exhibits icosahedral symmetry and comprise 72 capsomers.

Currently, there are over 90 different types of HPV, mainly causing papillary disease in the skin and mucosa of human. HPV types are divided into three groups depending on their relation with tumorigenesis: (1) group of low or no cancerogenic risk, containing types 6, 11, 39, 41, 42, and 55; (2) group of medium cancerogenic risk, containing types 31, 33, 35, 51, and 52; and (3) group of high cancerogenic risk, containing types 16, 18, 45, and 56.

Epidemiological investigation reveals that HPV (such as HPV6, 11) infection in the anal-genital mucosa is the third most common sexually transmitted disease following trichomoniasis and chlamydia. Pathological changes caused by HPV types 6 and 11 account for about 90% of these cases. In America, HPV infection of genital meatus among women occurs most frequently when they are 15-25 years old and is highly related to the infected person's sexual behavior. In China, HPV infection among women occurs most frequently when they are 20-29 years old, and the infection rate is 1606.1/100,000. Women are less infected with HPV as they grow older than 35. However, since the majority of HPV infections are sub-clinical, it is difficult to accurately estimate the infection rate. As estimated by the US CDC, the risk is approximately 10% during the whole life. In addition, there is little data regarding HPV infection among men, due to the difficulty of sample collection and the lesser severity of consequences. Currently, HPV infection rate among men is believed to be close to the one among women. In the United States, condyloma acuminatum can be found in 1% of sexually active adult men. Therefore, the development of a safe, efficient vaccine for HPV 6 and 11 would be an effective way to prevent sexually transmitted diseases.

HPV L1 protein, with a molecular weight of 55-60 kDa, is the major capsid protein of the human papillomavirus and the main target protein of the HPV vaccine. HPV L1 protein expressed in multiple different expression systems can form Virus-like particles (VLPs) which resemble native HPV particles morphologically, without the assistance of the L2 protein. The VLP, consisting of 72 pentamers of the L1 proteins, exhibits icosahedral symmetry. Since the VLPs retain the native epitopes of the viral particles, they are highly immunogenic and can induce the generation of neutralizing antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral DNA. Therefore, VLP vaccines become the primary candidate for an HPV vaccine.

The key for development of a vaccine is to efficiently produce VLP vaccines of HPV in large-scale. Currently, the most commonly used expression systems are eukaryotic expression systems and prokaryotic expression systems.

The commonly used eukaryotic systems comprise poxvirus, insect baculovirus and yeast vectors. HPV L1 protein expressed in eukaryotic systems shows little conformational difference from that of the native virus, and can self-assemble into VLPs. Thus, purified VLPs can be easily obtained after gradient density centrifugation. It brings a lot of convenience to the purification work. However, due to the high culture costs and low expression level, it is quite difficult to product industrially on a large-scale. The HPV vaccine Gardasil®, which came into the market recently, is more expensive than others due to low expression level and high production cost of the Saccharomyces cerevisiae expression system employed in its manufacture.

The expression of HPV L1 protein in a prokaryotic system such as E. coli has been previously reported. Banks, Matlashewski, et al. published a paper regarding the expression of HPV 16 L1 by employing E. coli (Banks, L., G Matlashewski, et al. (1987). J Gen Virol 68 (Pt 12): 3081-9). However, most HPV L1 proteins expressed by E. coli lose their native conformation and cannot induce the generation of protective antibodies against HPV. Alternatively, although HPV VLPs can be obtained from the incorrectly folded proteins by steps such as purification from inclusion bodies and refolding, it is difficult to apply this method to large-scale production, as the protein is largely lost during the refolding process and the yield is low (Kelsall, S. R. and J. K. Kulski (1995). J Virol Methods 53(1): 75-90). Although HPV L1 protein may be expressed in a soluble form with a correct conformation in E. coli and dissolved in the supernatants of E. coli lysate, the expression level is low. Moreover, since there are large number and amount of impure proteins, it is difficult to isolate the proteins of interest from them. Although it is reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to large-scale production because expensive enzymes are required to cleave the fusion protein.

Therefore, a HPV L1 protein capable of inducing the generation of protective antibodies against HPV, and a virus-like particle consisting of the same are still needed in the art, so

DESCRIPTION OF THE INVENTION

This invention aims to provide a novel HPV type 6 L1 protein, the virus-like particles (VLPs) consisting of it, and a vaccine comprising the VLPs.

During research, it was found by chance that the *E. coli* expression system can produce a truncated HPV 6 L1 protein that can induce the generation of neutralizing antibodies against HPV 6. After purification, the truncated HPV6 L1 protein can be produced in high yield, with at least 50% purity. Further treatment of the purified HPV L1 protein can produce VLPs, which can induce the production of neutralizing antibodies against HPV6. The invention has been completed based on the above.

Therefore, the first aspect of the invention relates to HPV 6 L1 proteins with 2, 3, 4, or 5 amino acids truncated at N-terminal as compared to a wild type HPV 6 L1 protein. Preferably, the truncated protein has the sequence set forth in SEQ ID Nos:1, 2, 3, or 4, especially the sequence set forth in SEQ ID NO:1.

A further aspect of the invention relates to a polynucleotide encoding the truncated protein according to the invention, and a vector containing the polynucleotide.

A further aspect of the invention relates to a cell comprising the vector.

The invention also relates to a composition comprising the truncated protein, the polynucleotide, the vector, or the cell.

A further aspect of the invention relates to a HPV 6 VLP, comprising or consisting of a HPV 6 L1 protein with 2, 3, 4, or 5 amino acids truncated at the N terminal such as a HPV 6 L1 protein having a sequence set forth in SEQ ID NOs: 1, 2, 3, or 4.

A further aspect of the invention relates to a method for obtaining the HPV 6 L1 protein, comprising the expression of a truncated HPV 6 L1 gene fragment in an *E. coli* system and the subsequent purification of the protein from the lysate supernatant.

In a preferred embodiment of the invention, a method for obtaining HPV 6 L1 protein comprises:
a) expressing the truncated HPV 6 L1 gene fragment in a *E. coli* expression system;
b) disrupting *E. coli*, which has expressed the truncated HPV 6 L1 protein, in a salt solution at a concentration of from 100 mM to 600 mM, and isolating the supernatant;
c) decreasing the salt concentration of the supernatant in b) to from 100 mM to 0, inclusive, by using water or a low salt solution, and collecting a precipitate;
d) redissolving the precipitation in c) in a salt solution at a concentration of from 150 mM to 2500 mM, with a reductant added, and then isolating the resultant solution, wherein the solution contains the truncated HPV 6 L1 protein with a purity of at least 50%.

More generally, the invention also relates to a method for obtaining a HPV L1 protein, such as the HPV 6 L1 protein according to the invention, comprising:
a) expressing a HPV L1 gene encoding the HPV L1 protein in an *E. coli* expression system;
b) disrupting *E. coli*, which has expressed the HPV L1 protein, in a salt solution at a concentration of from 100 mM to 600 mM, and isolating the supernatant;
c) decreasing the salt concentration of the supernatant in b) to from 100 mM to 0, inclusive, by using water or a low salt solution, and collecting a precipitate;
d) redissolving the precipitation of c) in a salt solution at a concentration of from 150 mM to 2500 mM, with a reductant added, and then isolating the resultant solution, wherein the solution contains the HPV L1 protein with a purity of at least 50%.

The invention also relates to a vaccine for the prevention of condyloma acuminatum or HPV infection, comprising VLPs of HPV 6 L1 proteins according to the invention. Preferably, the vaccine further comprises at least one VLPs selected from VLPs of HPV 18, 11, 16, 31, 33, 45, 52, and 58 L1 proteins. Generally, the vaccine further contains excipients or vectors for vaccine.

Preferably, the vaccine comprises HPV 6 VLPs and HPV 11 VLPs, especially the HPV 6 VLPs comprising or consisting of a protein having an amino acid sequence set forth in SEQ ID No: 4, and the HPV 11 VLPs comprising or consisting of a protein having an amino acid sequence set forth in SEQ ID No: 7. More preferably, the vaccine further comprises HPV 16 VLPs and HPV 18 VLPs, especially the HPV 16 VLPs comprising or consisting of a protein having an amino acid sequence set forth in SEQ ID No: 8, and the HPV 18 VLPs comprising or consisting of a protein having an amino acid sequence set forth in SEQ ID No: 9.

In a specially preferred embodiment, the vaccine comprises the HPV 6 VLPs comprising or consisting of a protein having an amino acid sequence set forth in SEQ ID No: 4, the HPV 11 VLPs comprising or consisting of a protein having an amino acid sequence set forth in SEQ ID No: 7, the HPV 16 VLPs comprising or consisting of a protein having an amino acid sequence set forth in SEQ ID No: 8, and the HPV 18 VLPs comprising or consisting of a protein having an amino acid sequence set forth in SEQ ID No: 9.

The invention further relates to the use of the HPV 6 L1 protein or the VLPs thereof in the manufacture of a vaccine for the prevention of condyloma acuminatum or HPV infections.

The invention further relates to a method for preventing condyloma acuminatum or HPV infections, comprising administrating a vaccine comprising an preventively effective amount of HPV 6 L1 protein to a human or animal in need of preventing condyloma acuminatum or HPV infections.

The invention involves a method for obtaining VLPs of the HPV 6 L1 protein, comprising:
e) further purifying the truncated HPV 6 L1 protein with a purity of at least 50% by subjecting it to a chromatography;
f) removing the reductant from the HPV 6 L1 protein obtained in e).

This invention involves a method for preparing a vaccine for preventing condyloma acuminatum or HPV infections, comprising blending the VLPs above, and optionally, one or more VLPs selected from the group consisting of VLPs of HPV 11, 16, 18, 31, 33, 45, 52 and 58, with carriers or excipients useful for vaccines.

Definitions of the Term in Present Invention

According to the invention, the term "*E. coli* expression system" refers to a expression system consisting of *E. coli* (strains) and vectors, wherein the *E. coli* (strains) include, but are not limited to: GI698, ER2566, BL21 (DE3), B834 (DE3), and BLR (DE3), which are available on the market.

According to the invention, the term "vectors" refers to the nucleic acid carrier tools which can have a polynucleotide encoding a protein inserted therein and allow for the expression of the protein. The "vector" can have the carried genetic material expressed in a host cell by transformation, transduction, and transfection into the host cell. For example, "vectors" include plasmids, phages, cosmids and the like.

According to the invention, the term "a gene fragment of a truncated HPV 6 L1 protein" refers to the nucleic acids with the nucleotide(s) encoding one or more amino acid sequences deleted at 5' or 3' terminal of the wild-type HPV 6 L1 gene (cDNA). The full-length gene sequence of the wild-type HPV 6 L1 gene can be found in, but not limited to, the following NCBI sequences: AF067042.1, AF092932.1, L41216.1 and X00203.1.

The term "truncated HPV 6 L1 protein" refers to the protein with one or more amino acids deleted at the N- and/or C-terminal of the wild-type HPV 6 L1 protein. The full-length gene sequence of the wild-type HPV 6 L1 protein can be found in, but not limited to, the full-length L1 proteins encoded by the following NCBI sequences: AF067042.1, AF092932.1, L41216.1 and X00203.1.

According to the invention, the term "carriers and excipients useful for vaccines" refers to one or more reagents, including but not limited to: pH regulators, surfactants, adjuvants, and ionic strength enhancers. For example, pH regulators include, but are not limited to, phosphate buffers; surfactants include, but are not limited to: anion surfactants, cation surfactants, non-ionic surfactants (for example, but not limited to Tween-80); adjuvants include, but are not limited to, aluminum hydroxide and Freund's complete adjuvant; and Ionic strength enhancers include, but are not limited to, NaCl.

According to the invention, the term "chromatography" includes, but is not limited to: ion exchange chromatography (e.g. cation-exchange chromatography), hydrophobic interaction chromatography, absorbant chromatography (e.g. hydroxyapatite chromatography), gel filtrate chromatography (gel exclusion chromatography), and affinity chromatography.

According to the invention, the truncated HPV 6 L1 proteins may be obtained preferably by the following steps:
 a) disrupting *E. coli*, which expresses truncated HPV 6 L1 protein, in a buffer containing 100-600 mM salt, preferably 200-500 mM;
 b) isolating the supernatant from the disrupted solution, then decreasing the salt concentration of the supernatant to 100 mM-0 M with water or a low-salt buffer (generally, with a salt concentration lower than the one of the buffer for disrupting);
 c) separating a precipitant from the supernatant with a salt concentration as low as 100 mM-0;
 d) redissoving the precipitant in a solution containing a reductant and having a salt concentration of 150-2000 mM, preferably greater than 200 mM;
 e) isolating a solution of the truncated HPV 6 L1 proteins with a purity of at least 50%, preferably at least 70%, more preferably at least 80%.

According to the invention, in the method for obtaining the truncated HPV 6 L1 proteins, the term "buffer" refers to a solution which can maintain pH value stable within a certain range, including but not limited to: Tris buffers, phosphate buffers, HEPES buffers, and MOPS buffers.

According to the invention, the disrupting of the prokaryotic host cell can be achieved by methods including, but not limited to one or more of homogenizer disrupting, ultrasonic treatment, grinding, high pressure extrusion, and lysozyme treatment.

According to the invention, in the method for obtaining the truncated HPV 6 L1 proteins, the salts used include, but are not limited to: one or more of neutral salts, especially alkali metal salt, ammonium salts, hydrochlorides, sulfates, bicarbonates, phosphate salts or hydrogenphosphates, espeically NaCl, KCl, $NH_4Cl$, $(NH_4)_2SO_4$. NaCl are preferred. The reductant used includes, but is not limited to, DTT and 2-mercaptoethanol, in an amount of including, but not limited to, 10-100 mM.

According to the invention, the VLPs of the truncated HPV 6 L1 protein may be produced by the following steps: further purifying the truncated HPV 6 L1 protein with a purity of at least 50% by subjecting it to a chromatography, and thereby obtaining a purified truncated HPV 6 L1 protein solution; and removing the reductant from the purified HPV 6 L1 protein solution, and thereby obtaining VLPs of the truncated HPV 6 L1. Methods for removing the reductant include, but are not limited to, known techniques in the art, such as dialysis, ultrafiltration, and chromatography.

According to the invention, the truncated HPV L1 protein preferably has the sequence set forth in SEQ ID NO:1.

According to the invention, the vaccine may be administrated in a patient-acceptable form, including but not limited to oral and injection, preferably injection.

According to the invention, the vaccine is preferably used in a unit dose. Each unit dose contains 5-80 μg truncated HPV 6 L1 VLP, preferably 20-40 μg.

Beneficial Effect

Presently, the expression systems useful for preparing HPV VLPs include eukaryotic and prokaryotic expression systems.

HPV L1 proteins expressed in eukaryotic expression systems retain their native conformation, and can form VLPs on their own. In most cases, VLP with a correct conformation can be obtained by simple purification. Nevertheless, eukaryotic expression systems, such as the baculovirus and yeast expression systems, are difficult to be applied in large-scale industrial production due to low expression levels and high costs.

Prokaryotic expression systems, such as *E. coli* systems, have the advantages of high expression levels at a lower cost. However, when expressed in a prokaryotic system, the HPV L1 protein usually loses its native conformation and is expressed in a form of inclusion bodies in the precipitant. Renaturation of the protein from inclusion bodies is still a problem worldwide. Due to the difficulty and inefficiency of renaturation, this method is limited to small-scale lab research and cannot be applied on a large scale so as to obtain VLP with a correct conformation from the inclusive bodies. Although the HPV L1 protein can exist in its native conformation in the supernatant of *E. coli* lysate, its expression levels are low. Moreover, it is quite difficult to purify the HPV L1 protein from the numerous soluble proteins in the *E. coli* lysate supernatant. Generally, the purification is completed by means such as fusion expression and affinity chromatography which are not feasible for industrial-scale processes due to expensive enzymes employed therein.

In this invention, N-truncated HPV 6 L1 protein is expressed in an *E. coli* expression system and is selectively precipitated from the *E. coli* lysate supernatant under mild conditions. The HPV 6 L1 protein is then redissolved in a salt buffer to significantly improve its purity while still retaining its native conformation. The redissolved protein of interest can be immediately subjected to ion-exchange or hydrophobic interaction chromatography so as to obtain the pure protein. The purified, truncated HPV 6 L1 protein obtained from these steps, can self-assemble into VLPs with good immunogenicity and the ability to induce neutralizing antibodies of a high titer against HPV 6, which is a good vaccine for preventing human from HPV 6 infection. In addition, the truncated HPV 6 L1 protein used in the present invention, with the antigenicity and particle-selfassembly ability of the full-length HPV 6 L1 protein retained, is easily expressed in an *E. coli* expression system, and can be economically purified without using expensive enzymes. Furthermore, because the protein of interest is not subjected to the intensive procedures of denaturation and renaturation during purification, the method can be applied industrially on a large scale due to low loss.

The invention will be more apparent after referring to the detailed description and the drawings as follows. All public references are incorporated hereby by reference in their entirety.

DESCRIPTION OF DRAWINGS

FIG. 10 the transmission electron microscopy (TEM) photographs of the VLPs of HPV6N2C-L1, HPV6N4C-L1 and HPV6N5C-L1 protein separately having 2, 4 and 5 amino acids truncated at the N-terminal of HPV 6 L1 protein obtained after steps a)-f), taken at 50,000× magnification. 1. The transmission electron microscopy (TEM) photographs of HPV6N2C-L1 VLPs obtained after steps a)-f), taken at 50,000× magnification. 2 The transmission electron microscopy (TEM) photographs of HPV6N4C-L1 VLPs obtained after steps a)-f), taken at 50,000× magnification. 3. The transmission electron microscopy (TEM) photographs of HPV6N5C-L1 VLPs obtained after steps a)-f), taken at 50,000× magnification. The results show that a great deal of VLPs in a radius of about 25 nm were observed in visual field, wherein the particle size was consistant with the theoretic size and the particles were homogenous.

SEQUENCES

Figure 1:
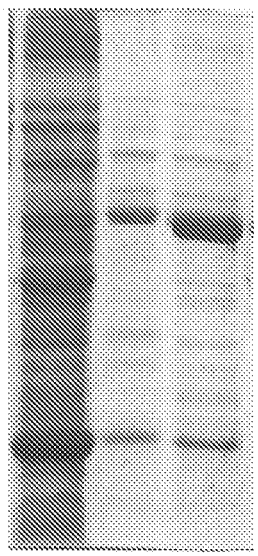
FIG. 1 shows the SDS-PAGE result of HPV6N3C-L1 protein during steps a)-d) of the method according to the invention. Lane 1: Lysate supernatant; Lane 2: HPV6N3C-L1 protein precipitated by tengenital flow; Lane 3: Redissolved HPV6N3C-L1 in a re-suspension solution. The result shows that the purity of HPV6N3C-L1 reached about 70% following the steps of precipitation and re-dissolution.

SEQ ID NO: 1:

```
  1 MPSDSTVYVP PPNPVSKVVA TDAYVTRTNI FYHASSSRLL
    AVGHPYFSIK RANKTVVPKV

61 SGYQYRVFKV VLPDPNKFAL PDSSLFDPTT QRLVWACTGL
    EVGRGQPLGV GVSGHPFLNK

121 YDDVENSGSG GNPGQDNRVN VGMDYKQTQL CMVGCAPPLG
    EHWGKGKQCT NTPVQAGDCP

181 PLELITSVIQ DGDMVDTGFG AMNFADLQTN KSDVPIDICG
    TTCKYPDYLQ MAADPYGDRL

241 FFFLRKEQMF ARHFFNRAGE VGEPVPDTLI IKGSGNRTSV
    GSSIYVNTPS GSLVSSEAQL

301 FNKPYWLQKA QGHNNGICWG NQLFVTVVDT TRSTNMTLCA
    SVTTSSTYTN SDYKEYMRHV

361 EEYDLQFIFQ LCSITLSAEV VAYIHTMNPS VLEDWNFGLS
    PPPNGTLEDT YRYVQSQAIT
```

```
421 CQKPTPEKQK PDPYKNLSFW EVNLKEKFSS ELDQYPLGRK
    FLLQSGYRGR SSIRTGVKRP
481 AVSKASAAPK RKRAKTKR
SEQ ID NO: 2
  1 MRPSDSTVYV PPPNPVSKVV ATDAYVTRTN IFYHASSSRL
    LAVGHPYFSI KRANKTVVPK
 61 VSGYQYRVFK VVLPDPNKFA LPDSSLFDPT TQRLVWACTG
    LEVGRGQPLG VGVSGHPFLN
121 KYDDVENSGS GGNPGQDNRV NVGMDYKQTQ LCMVGCAPPL
    GEHWGKGKQC TNTPVQAGDC
181 PPLELITSVI QDGDMVDTGF GAMNFADLQT NKSDVPIDIC
    GTTCKYPDYL QMAADPYGDR
241 LFFFLRKEQM FARHFFNRAG EVGEPVPDTL IIKGSGNRTS
    VGSSIYVNTP SGSLVSSEAQ
301 LFNKPYWLQK AQGHNNGICW GNQLFVTVVD TTRSTNMTLC
    ASVTTSSTYT NSDYKEYMRH
361 VEEYDLQFIF QLCSITLSAE VVAYIHTMNP SVLEDWNFGL
    SPPPNGTLED TYRYVQSQAI
421 TCQKPTPEKQ KPDPYKNLSF WEVNLKEKFS SELDQYPLGR
    KFLLQSGYRG RSSIRTGVKR
481 PAVSKASAAP KRKRAKTKR
SEQ ID NO: 3
  1 MSDSTVYVPP PNPVSKVVAT DAYVTRTNIF YHASSSRLLA
    VGHPYFSIKR ANKTVVPKVS
 61 GYQYRVFKVV LPDPNKFALP DSSLFDPTTQ RLVWACTGLE
    VGRGQPLGVG VSGHPFLNKY
121 DDVENSGSGG NPGQDNRVNV GMDYKQTQLC MVGCAPPLGE
    HWGKGKQCTN TPVQAGDCPP
181 LELITSVIQD GDMVDTGFGA MNFADLQTNK SDVPIDICGT
    TCKYPDYLQM AADPYGDRLF
241 FFLRKEQMFA RHFFNRAGEV GEPVPDTLII KGSGNRTSVG
    SSIYVNTPSG SLVSSEAQLF
301 NKPYWLQKAQ GHNNGICWGN QLFVTVVDTT RSTNMTLCAS
    VTTSSTYTNS DYKEYMRHVE
361 EYDLQFIFQL CSITLSAEVV AYIHTMNPSV LEDWNFGLSP
    PPNGTLEDTY RYVQSQAITC
421 QKPTPEKQKP DPYKNLSFWE VNLKEKFSSE LDQYPLGRKF
    LLQSGYRGRS SIRTGVKRPA
481 VSKASAAPKR KRAKTKR
SEQ ID NO: 4
  1 MDSTVYVPPP NPVSKVVATD AYVTRTNIFY HASSSRLLAV
    GHPYFSIKRA NKTVVPKVSG
 61 YQYRVFKVVL PDPNKFALPD SSLFDPTTQR LVWACTGLEV
    GRGQPLGVGV SGHPFLNKYD
121 DVENSGSGGN PGQDNRVNVG MDYKQTQLCM VGCAPPLGEH
    WGKGKQCTNT PVQAGDCPPL
181 ELITSVIQDG DMVDTGFGAM NFADLQTNKS DVPIDICGTT
    CKYPDYLQMA ADPYGDRLFF
241 FLRKEQMFAR HFFNRAGEVG EPVPDTLIIK GSGNRTSVGS
    SIYVNTPSGS LVSSEAQLFN
301 KPYWLQKAQG HNNGICWGNQ LFVTVVDTTR STNMTLCASV
    TTSSTYTNSD YKEYMRHVEE
361 YDLQFIFQLC SITLSAEVVA YIHTMNPSVL EDWNFGLSPP
    PNGTLEDTYR YVQSQAITCQ
421 KPTPEKQKPD PYKNLSFWEV NLKEKFSSEL DQYPLGRKFL
    LQSGYRGRSS IRTGVKRPAV
481 SKASAAPKRK RAKTKR
SEQ ID NO: 5
  1 ATGTGGCGGC CTAGCGACAG CACAGTATAT GTGCCTCCTC
    CTAACCCTGT ATCCAAAGTT
 61 GTTGCCACGG ATGCTTATGT TACTCGCACC AACATATTTT
    ATCATGCCAG CAGTTCTAGA
121 CTTCTTGCAG TGGGTCATCC TTATTTTTCC ATAAAACGGG
    CTAACAAAAC TGTTGTGCCA
181 AAGGTGTCAG GATATCAATA CAGGGTATTT AAGGTGGTGT
    TACCAGATCC TAACAAATTT
241 GCATTGCCTG ACTCGTCTCT TTTTGATCCC ACAACACAAC
    GTTTGGTATG GGCATGCACA
301 GGCCTAGAGG TGGGCAGGGG ACAGCCATTA GGTGTGGGTG
    TAAGTGGACA TCCTTTCCTA
361 AATAAATATG ATGATGTTGA AAATTCAGGG AGTGGTGGTA
    ACCCTGGACA GGATAACAGG
421 GTTAATGTTG GTATGGATTA TAAACAAACA CAATTATGCA
    TGGTTGGATG TGCCCCCCCT
481 TTGGGCGAGC ATTGGGGTAA AGGTAAACAG TGTACTAATA
    CACCTGTACA GGCTGGTGAC
541 TGCCCGCCCT TAGAACTTAT TACCAGTGTT ATACAGGATG
    GCGATATGGT TGACACAGGC
601 TTTGGTGCTA TGAATTTTGC TGATTTGCAG ACCAATAAAT
    CAGATGTTCC TATTGACATA
661 TGTGGCACTA CATGTAAATA TCCAGATTAT TTACAAATGG
    CTGCAGACCC ATATGGTGAT
```

```
 721 AGATTATTTT TTTTTCTACG GAAGGAACAA ATGTTTGCCA
     GACATTTTTT TAACAGGGCT
 781 GGCGAGGTGG GGGAACCTGT GCCTGATACT CTTATAATTA
     AGGGTAGTGG AAATCGAACG
 841 TCTGTAGGGA GTAGTATATA TGTTAACACC CCAAGCGGCT
     CTTTGGTGTC CTCTGAGGCA
 901 CAATTGTTTA ATAAGCCATA TTGGCTACAA AAAGCCCAGG
     GACATAACAA TGGTATTTGT
 961 TGGGGTAATC AACTGTTTGT TACTGTGGTA GATACCACAC
     GCAGTACCAA CATGACATTA
1021 TGTGCATCCG TAACTACATC TTCCACATAC ACCAATTCTG
     ATTATAAAGA GTACATGCGT
1081 CATGTGGAAG AGTATGATTT ACAATTTATT TTTCAATTAT
     GTAGCATTAC ATTGTCTGCT
1141 GAAGTAATGG CCTATATTCA CACAATGAAT CCCTCTGTTT
     TGGAAGACTG GAACTTTGGG
1201 TTATCGCCTC CCCCAAATGG TACATTAGAA GATACCTATA
     GGTATGTGCA GTCACAGGCC
1261 ATTACCTGTC AAAAGCCCAC TCCTGAAAAG CAAAAGCCAG
     ATCCCTATAA GAACCTTAGT
1321 TTTTGGGAGG TTAATTTAAA AGAAAAGTTT CTAGTGAAT
     TGGATCAGTA TCCTTTGGGA
1381 CGCAAGTTTT TGTTACAAAG TGGATATAGG GGACGGTCCT
     CTATTCGTAC CGGTGTTAAG
1441 CGCCCTGCTG TTTCCAAAGC CTCTGCTGCC CCTAAACGTA
     AGCGCGCCAA AACTAAAAGG
1501 TAA
SEQ ID NO: 6
   1 ATGCCTAGCG ACAGCACAGT ATATGTGCCT CCTCCTAACC
     CTGTATCCAA
  51 AGTTGTTGCC ACGGATGCTT ATGTTACTCG CACCAACATA
     TTTTATCATG
 101 CCAGCAGTTC TAGACTTCTT GCAGTGGGTC ATCCTTATTT
     TTCCATAAAA
 151 CGGGCTAACA AAACTGTTGT GCCAAAGGTG TCAGGATATC
     AATACAGGGT
 201 ATTTAAGGTG GTGTTACCAG ATCCTAACAA ATTTGCATTG
     CCTGACTCGT
 251 CTCTTTTTGA TCCCACAACA CAACGTTTGG TATGGGCATG
     CACAGGCCTA
 301 GAGGTGGGCA GGGGACAGCC ATTAGGTGTG GGTGTAAGTG
     GACATCCTTT
 351 CCTAAATAAA TATGATGATG TTGAAAATTC AGGGAGTGGT
     GGTAACCCTG
 401 GACAGGATAA CAGGGTTAAT GTTGGTATGG ATTATAAACA
     AACACAATTA
 451 TGCATGGTTG GATGTGCCCC CCCTTTGGGC GAGCATTGGG
     GTAAAGGTAA
 501 ACAGTGTACT AATACACCTG TACAGGCTGG TGACTGCCCG
     CCCTTAGAAC
 551 TTATTACCAG TGTTATACAG GATGGCGATA TGGTTGACAC
     AGGCTTTGGT
 601 GCTATGAATT TTGCTGATTT GCAGACCAAT AAATCAGATG
     TTCCTATTGA
 651 TATATGTGGC ACTACATGTA AATATCCAGA TTATTTACAA
     ATGGCTGCAG
 701 ACCCTTATGG TGATAGATTA TTTTTTTTTC TACGGAAGGA
     ACAAATGTTT
 751 GCCAGACATT TTTTTAACAG GGCTGGCGAG GTGGGGGAAC
     CTGTGCCTGA
 801 TACTCTTATA ATTAAGGGTA GTGGAAATCG AACGTCTGTA
     GGGAGTAGTA
 851 TATATGTTAA CACCCCAAGC GGCTCTTTGG TGTCCTCTGA
     GGCACAATTG
 901 TTTAATAAGC CATATTGGCT ACAAAAAGCC CAGGGACATA
     ACAATGGTAT
 951 TTGTTGGGGT AATCAACTGT TGTTACTGT GGTAGATACC
     ACACGCAGTA
1001 CCAACATGAC ATTATGTGCA TCCGTAACTA CATCTTCCAC
     ATACACCAAT
1051 TCTGATTATA AGAGTACAT GCGTCATGTG AAGAGTATG
     ATTTACAATT
1101 TATTTTTCAA TTATGTAGCA TTACATTGTC TGCTGAAGTA
     GTGGCCTATA
1151 TTCACACAAT GAATCCCTCT GTTTTGGAAG ACTGGAACTT
     TGGGTTATCG
1201 CCTCCCCCAA ATGGTACATT AGAAGATACC TATAGGTATG
     TGCAGTCACA
1251 GGCCATTACC TGTCAAAAGC CCACTCCTGA AAAGCAAAAG
     CCAGATCCCT
```

-continued

```
1301 ATAAGAACCT TAGTTTTTGG GAGGTTAATT TAAAAGAAAA
     GTTTTCTAGT
1351 GAATTGGATC AGTATCCTTT GGGACGCAAG TTTTTGTTAC
     AAAGTGGATA
1401 TAGGGGACGG TCCTCTATTC GTACCGGTGT TAAGCGCCCT
     GCTGTTTCCA
1451 AAGCCTCTGC TGCCCCTAAA CGTAAGCGCG CCAAAACTAA
     AAGGTAA
```

The description is further illustrated in combination with the Examples, wherein it is not limited to the Examples.

Example 1

Expression of the Truncated HPV6 L1 Protein (SEQ ID NO.1)

Preparation of HPV6 L1 Gene Fragments as PCR Template

The full-length gene of HPV-6 L1 was synthesized by Shanghai Boya Bio Co. The synthesized gene fragment has a full length of 1503 bp and has a sequence of SEQ ID NO:5. Based on the synthetic full-length gene fragment of HPV-6 L1, the truncated HPV 6 L1 protein according to the invention was prepared as a template.

Construction of Non-Fusion Expression Vector of Truncated HPV6 L1 gene

The full-length gene fragment of HPV-6 L1 synthesized in the previous step were used as the template for the next PCR reaction. The forward primer was 6N3F: 5'-CATATG CCT AGC GAC AGC ACA GTA TA-3' (SEQ ID NO:10), at the 5' terminal of which the restriction endonuclease NdeI site was introduced. The sequence of NdeI site was CAT ATG, wherein ATG was the initiation codon in E. coli system. The reverse primer was 6CR: 5'-GTCGAC TTA CCT TTT AGT TTT GGC GC-3' (SEQ ID NO:11), at the 5' terminal of which the restriction endonuclease SalI site was introduced. Amplification was performed in a Biometra T3 PCR thermocycler using the following parameters:

| | |
|---|---|
| 94° C. denaturation 5 min | 1 cycle |
| 94° C. denaturation 50 sec | 25 cycles |
| 57° C. annealing 50 sec | |
| 72° C. elongation 2 min | |
| 72° C. elongation 10 min | 1 cycle |

The DNA fragments, about 1.5 kb in length, were obtained after amplification. The PCR products were linked to the pMD 18-T vector (Takara Biosciences). After digestion with NdeI/SalI, it was identified that positive colonies, wherein the truncated HPV6 L1 gene was inserted, were obtained, designated as pMD 18-T-HPV6N3C-L1.

The nucleotide sequence of interest, which was inserted into the plasmid pMD 18-T-HPV6N3C-L1, was determined as SEQ ID NO: 6 by Shanghai Boya Bio Co. through using M13+/− primers. SEQ ID NO:6 encodes the amino acid sequence set forth in SEQ ID NO:1 which corresponds to a HPV 6 L1 protein having 3 amino acids truncated at its N-terminal and no amino acid truncated at its C-terminal and was designated as HPV6N3C-L1.

The truncated HPV6N3C-L1 gene fragments were obtained by NdeI/SalI digestion of plasmid pMD 18-T-HPV6N3C-L1. The fragments were linked to the prokaryotic expression vector pTrxFus digested with NdeI/SalI (Invitrogen). Since the fusion protein was cleaved, the protein of interest was expressed immediately after initiating the expression of the amino acid Met, without other fusion proteins included. Colonies were screened with NdeI/SalI digestion. Positive colonies containing the insert of the L1 gene fragment were labeled pTRX-HPV6N3C-L1. 1 µL plasmid pTRX-HPV6N3C-L1 (0.15 mg/ml) was used to transform 40 µL competent E. coli GI698 (Invitrogen) prepared by Calcium chloride method, and then were coated on solid CAA media (dissolving 6 g $Na_2HPO_4$, 3 g $KH_2PO_4$, 0.5 g NaCl, 1 g $NH_4Cl$, 20 g casein hydrolysate, 0.095 $MgCl_2$, 1.5 g agar powder, and 20 ml 50% glycerin in 900 ml deionized water, and was added) containing benzyl chloride (at a final concentration of 100 mg/ml, the same as below). Plates were incubated at 30° C. for about 10-12 h until single colonies could be observed clearly. Single colonies from the plates were transferred to a tube containing 4 ml liquid IMC medium containing benzyl chloride. Cultures were incubated in a shaking incubator at 220 rpm for 10 h at 25° C., and then 1 ml bacterial solution was freeze-dried and stored at −70° C.

Expression of HPV6N3C-L1 in Large Scale

E. coli transformed with pTRX-HPV6N3C-L1 was taken from freeze-dried stain at −70° C., and diluted with a little sterile water, and then incubated in 50 mL IMC medium containing benzyl amine at 200 rpm and 30° C. for 8 h. Then, the cultures were transferred to ten flasks (5 ml cultures per flask), each of which contains 500 mL LB medium, and were incubated in a shaking incubator overnight at 200 rpm and 30° C.

A 50 L fermenter made by Shanghai Baoxing Biological Ltd was used in large-scale incubation. pH electrode was calibrated. 30 L LB medium was prepared and transferred into the fermenter, sterilized at 121° C. for 30 minutes. Dissolved oxygen electrode was calibrated, wherein the value was determined as 0 before introduction of air after sterilization and as 100% prior to vaccintation after introduction of air while stirring at 100 rpm at the beginning.

Preparation of the feed: 30 g casein hydrolysates was dissolved in 100 mL deionized water to prepare a solution (30%), and 50 g glucose was dissolved in 100 ml deionized water to prepared a glucose solution (50%). The two mixtures were sterilized at 121° C. for 20 min.

On the second day, the starter cultures in the ten flasks (for a total of 5 L) were transferred to the fermenter. At 30° C. and pH 7.0, the dissolved $O_2$ was maintained at >40% by regulating agitation rate or air supply manually.

Flow Feed: 50% glucose and 30% casein hydrolysates were mixed at a 2:1 mass ratio.

Flow rates were as follows:
25 ml/min was defined as 100%.
1 h: 5%
2 h: 10%
3 h: 20%
4 h: 40%
5 h to the end: 60%

When $OD_{600}$ reached about 10.0, the culture temperature was lowered to 25° C. and 4 g tryptophan was added to begin an induction culture of 4 h. Fermentation was halted when $OD_{600}$ reached about 40. The culture was then centrifuged to obtain strains (about 2.5 kg).

IMC medium (1 liter):

| | |
|---|---|
| Na$_2$HPO$_4$ | 6 g |
| KH$_2$PO$_4$ | 3 g |
| NaCl | 0.5 g |
| NH$_4$Cl | 1 g |
| Casein Hydrolysates | 20 g |
| MgCl$_2$ | 0.095 g |

Example 2

Preparation of HPV6N3C-L1 with a Purity of about 70%

1 g strains were re-suspended in 10 ml lysis buffer (20 mM tris buffer pH 7.2, 300 mM NaCl). Strains were disrupted by passing through a APV homogenizer (Invensys Group) for five times at a pressure of 600 bar. The homogenate was centrifuged at 30,000 g (13,500 rpm in JA-14 rotor) for 15 min. The supernatant was subjected to SDS-PAGE on a 10% gel. At this stage, the HPV6N3C-L1 had a purity of about 10%. The supernatant was dialyzed by a Centrasette 5 Tangential Flow Filter (Pall Co.) running at a pressure of 0.5 psi, a flow rate of 500 ml/min, and a tangential flow rate of 200 mL/min, wherein the retention molecular weight was 30 kDa, the dialysate was 10 mM phosphate buffer pH 6.0, and the dialysis volume was three times as large as the volume of supernatant. After thorough dialysis, the mixture was centrifuged at 12,000 g (9500 rpm in JA-10 rotor (Beckman J25 high speed centrifuge)) for 20 min, and the precipitation was collected. The precipitation was re-suspended in 10 mM phosphate buffer pH 7.0 containing 10 mM DTT and 300 mM NaCl, wherein the volume of the buffer was 1/10 times as large as the volume of the supernatant. The mixture was stirred for 30 min and centrifuged at 30,000 g (13,500 rpm in JA-14 rotor (Beckman J25 high speed centrifuge)) for 20 min. The supernatant passes through a 0.22 μm filter membrane. The sample was further subjected to cation exchange chromatography. 300 μL of 6× loading buffer was added to 150 μL of the filtered supernatant, and the result solution was mixed. After heating in a water bath at 80° C. for 10 min, 10 ul of the sample was subjected to SDS-PAGE on a 10% gel at 120V for 120 min. The electrophoretic bands were stained by Coomassie brilliant blue. The result was shown in FIG. 1. According to the analysis of SDS-PAGE, HPV6N3C-L1 protein was purified and enriched after the steps of precipitation and re-dissolution, with the purity of about 70%.

Example 3

Chromatography Purification of HPV6N3C-L1

Purification of HPV6N3C-L1 by Cation exchange Chromatography
Equipment: AKTA Explorer 100 preparative liquid chromatography system (GE Healthcare, i.e. the original Amershan Pharmacia Co.)
Chromatographic media: SP Sepharose 4 Fast Flow
Column Volume: 5.5 cm×20 cm
Buffer: 20 mM phosphate buffer pH 7.0, 10 mM DTT
20 mM phosphate buffer pH 7.0, 10 mM DTT, 2M NaCl
Flow Rate: 25 mL/min
Detector Wavelength: 280 nm
Sample: 3 L 70% pure HPV6N3C-L1 solution Elution protocol: eluting undesired proteins with 200 mM NaCl, eluting the protein of interest with 500 mM NaCl, collecting 500 mM NaCl elutate, and finally getting about 900 mL purified HPV6N3C-L1 sample.

Purification of HPV6N3C-L1 by CHT-II Chromatography
Equipment: AKTA Explorer 100 preparative liquid chromatography system (GE Healthcare, i.e. the original Amershan Pharmacia Co.)
Chromatographic media: CHT-II (Bio-Rad)
Column Volume: 5.5 cm×20 cm
Buffer: 10 mM phosphate buffer pH7.0, 10 mM DTT, 0.5M NaCl
Flow Rate: 20 mL/min
Detector Wavelength: 280 nm
Sample: 500 mM NaCl elutate from SP Sepharose 4 Fast Flow
Elution protocol: directly collecting the pass-through containing the protein of interest.

Figure 2:
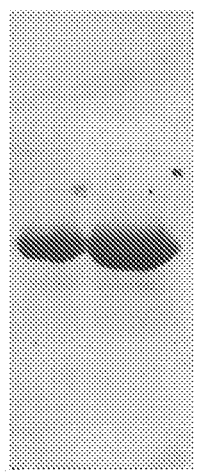
FIG. 2 shows the SDS-PAGE result of HPV6N3C-L1 that was obtained in step d) and was further purified according to step e). Lane 1: HPV6N3C-L1 purified according to step e), 10 μL; Lane 2: HPV6N3C-L1 purified according to step e), 20 μL. The result shows that HPV6N3C-L1 purified according to step e) reached a purity of about 98%.

The pass-through, which contains HPV6N3C-L1, was collected and about 1000 mL purified HPV6N3C-L1 was obtained. 30 μL 6× loading buffer was added to 150 μL HPV6N3C-L1 sample purified according to the method of the Example, and then the result solution was mixed thoroughly. After heating the solution in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 2. The concentration of the protein of interest was about 0.7 mg/ml, and the purity was greater than 98% according to SDS-PAGE.

Example 4

Assembly of HPV6N3C-L1 VLPs

Equipment: Centrasette 5 Tangential Flow Filter (Pall Co.), retention MW 30 kDa.
Sample: 1000 mL HPV6N3C-L1 obtained in Example 3
Sample Concentration: Sample was concentrated to 800 mL with the system tangential flow rate was adjusted to 50 mL/min
Sample renaturation: Sample Renaturation: Sample buffer was exchanged with 10 L renaturation buffer (20 mM PB pH 6.0, 2 mM CaCl$_2$, 2 mM MgCl$_2$, 0.5M NaCl, 0.003% Tween-80) thoroughly. When running the Tangential Flow Filter, the pressure was 0.5 psi and the tangential flow rate was 10 mL/min. When exchange was finished, the sample buffer was replaced with storage buffer (20 L PBS: 20 mM PB pH 6.5, 0.5M NaCl). The exchange volume was 20 L. The running pressure was 0.5 psi and the tangential flow rate was 25 mL/min. When the liquid exchange was finished, the sample was aseptically filtrated with a Pall filter (0.20 μm), and thereby obtaining HPV6N3C-L1 VLPs. The HPV6N3C-L1 VLPs were stored at 4° C. for further use.

Example 5

Determination of the Morphology and Immunogenicity of HPV6N3C-L1 VLPs

Figure 3:
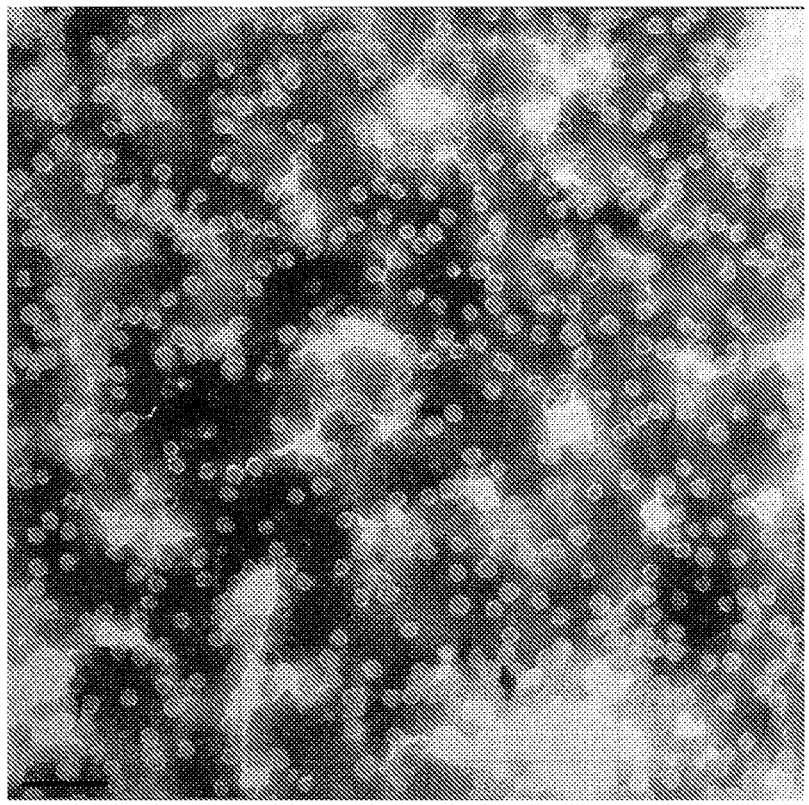
FIG. 3 shows the transmission electron microscopy (TEM) photograph of HPV6N3C-L1 VLPs obtained in step f), taken at 50,000× magnification. A great deal of VLPs in a radius of about 25 nm were observed in visual field, wherein the particle size was consistant with the theoretic size and the particles were homogenous.

Transmission Electron Microscopy (TEM) of HPV6N3C-L1 VLPs
The equipment was a JEOL 100 kV Transmission Electron Microscope (100,000× magnification). HPV6N3C-L1 VLPs were negatively stained with 2% phosphotungstic acid at pH 7.0, and fixed on a copper grid. Results were shown in FIG. 3.

It could be seen that the VLPs obtained in Example 4 had a radius of approximately 25 nm, and were homogenous and in a hollow form.

Dynamic Light-Scattering Measurement of HPV6N3C-L1 VLPs

Figure 4:
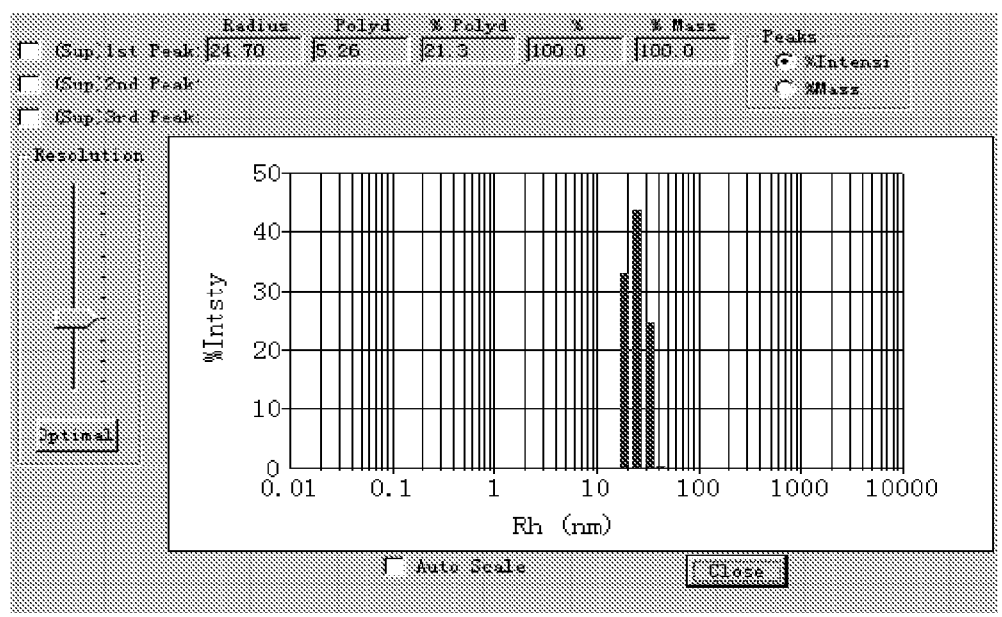
FIG. 4 shows the dynamic light-scattering measurement result of HPV6N3C-L1 VLPs obtained in step f). The result shows that HPV6N3C-L1 VLP had a hydrodynamic radius of 24.70 nm and a particle assembly rate of 100%.

DynaPro MS/X dynamic light-scattering instrument (including a temperature controller) (US Protein Solutions Co.) was used for light-scattering measurements. The regulation algorithm was used in the measurements. The sample was the one obtained in Example 4. The sample was passed through a 0.22 μm filter membrane prior to the measurement. Results were shown in FIG. 4. The result shows that HPV6N3C-L1 VLPs had a Hydrodynamic radius of 25.46 nm.

Establishment a Model of Pseudovirion Neutralization Assay for HPV6:

HPV can hardly be cultured in vitro, and the HPV host had a strong specificity. Thus, HPV can hardly be propagated in hosts other than human. That is, there was not an appropriate animal model for HPV. Therefore, in order to evaluate the immune productivity of HPV vaccine quickly, there was a need to establish a efficient model for in vitro neutralization assays.

In Vitro Infection Model of Pseudovirion: According to the characteristic that HPV VLP can package nucleic acids non-specifically, HPV pseudivirion was formed by expressing HPV L1 and L2 protein in cells, and by packaging viral DNA of episome or introducing reporter plasmids heterologously. Methods include expression systems based on recombinant viruses and cotransfection of multi-plasmids (see Yeager, M. D, Aste-Amezaga, M. et al (2000) Virology (278) 570-7).

The invention utilizes cotransfection of a multi-plasmid system. Some improvements were made as follows. An optimized calcium phosphate transfection method was established for the 293FT cell line, with a transfection efficiency of above 90%, which facilitate the production on a large scale. The resultant codon-optimized expression plasmid of HPV protein could express HPV L1 and L2 gene efficiently in mammalian cell lines, facilitating efficient assembly of pseudovirion.

1. Construction of HPV Pseudovirion:

P6L1h, p6L2h and pN31-EGFP (donated by Professor John T. Schiller of NIH) contain genes for HPV6L1, HPV6L2, and GFP, respectively. These plasmids were purified using CsCl density gradient centrifugation as described in The Molecular Cloning Experiment Guide, (3rd edition). The purification procedure was as follows:

Plasmids were used to transform *E. coli* DH5α;

Single colonies were transferred into 500 mL LB culture medium and incubated in a shaking flask at 37° C. for 16 h;

Culture medium was centrifuged at 9,000 g for 5 min and the stains were collected;

The following substances were successively added to bacteria in each 1000 mL LB: 40 mL solution I (50 mM glucose, 25 mM Tris-Cl pH 8.0, 10 mM EDTA pH 8.0) and 2 ml μg/μL RNase A), 40 mL solution II (0.2M NaOH, 1% SDS), and 48 mL solution III (60.0 mL 5M potassium acetate, 11.5 mL acetic acid, and 28.5 mL deionized water);

After placing on ice for 10 min, the mixture was centrifuged at 15,000 g for 20 min at 4° C.;

The supernatant was mixed with 0.6 volume of isopropyl alcohol, then was centrifuged again at 15,000 g for 30 min;

The supernatant was decanted into waste and the precipitation was washed with 70% ethanol;

The precipiation was dissolved in TE and the content of DNA was determined;

CsCl was dissolved in the solution of DNA (1 g DNA per 1.01 g CsCl), and then 100 μL 10 mg/mL EB solution was also dissolved in it;

The mixture was centrifuged using a Beckman NVT65 centrifuge at 62,000 rpm for 10 hr at 20° C.;

Closed circle DNA section was collected using an injector pinhead;

EB was extracted with equivalent volume of Isoamyl alcohol repeatedly for four times;

Three volumes of deionized water and eight volumes of dry ethanol were added to one volume of DNA solution, and then the mixture was centrifuged at 20000 g for 30 min at 4° C.;

The precipitation was collected and washed with 75% ethanol, and then dissolved in 1 mL TE;

The concentration of the DNA solution was determined, then the solution was stored in small packages at −20° C.

The purified p6L1h, p6L2h and pN31-EGFP co-transfected 293FT cells (Invitrogen) cultured on a 10 cm cell culture plate by calcium phosphate method. The calcium phosphate method was described as follows. 40 μg p6L1h, 40 μg p6L2h and 40 μg pN31-EGFP were separately added to the mixture of 1 mL HEPES solution (125 μL 1M HEPES/50 mL deionized water, at pH7.3 and 4° C.) and 1 mL 0.5M CaCl$_2$ solution. After mixing, 2 mL 2× HeBS solution (0.28M NaCl (16.36 g), 0.05M HEPES (11.9 g), 1.5 mM Na$_2$HPO$_4$ (0.213 g), dissolved in 1000 mL deionized water, at pH 6.96 and −70° C.) was added dropwise. After standing at room temperature for 1 min, the mixture was added to the 10 cm cell culture plate where the 293FT cells were cultured. The original culture medium was replaced with 10 ml complete medium (Invitrogen Co.) 6 hours later. 48 hours after transfection, the medium was decanted and the cells were washed twice with PBS. Then, the cells were collected and counted. Every 10$^8$ cells were suspended in 1 mL cytolytic solution (0.25% Brij58, 9.5 mM MgCl$_2$). After lysing, cell lysate was centrifugated at 5,000 g for 10 min and the supernatant was collected. The Pseudovirion solution was obtained after adding 5M NaCl to the supernatant to a final concentration of 850 mM, then was stored in small packages at −20° C.

293FT cells (Invitrogen) were spread on a 96-well cell culture plate (1.5×10$^4$ cells/well). Neutralization assay was performed five hours later. Serum samples were serially diluted with 10% DMEM half-by-half 50 μL diluted samples were separately mixed with 50 μL Pseudovirion solutions diluted with 10% DMEM (moi=0.1). After incubating at 4° C. for 1 h, the mixture was added to the 96-well cell culture plate spread with 293FT cells. The mixture was then incubated for 72 h at 37° C. Neutralization titers of samples were estimated by observing fluorescence. Infection percentage of cells in each well was checked by flow cytometry (EPICS XL, American Beckman Coulter Co.). The exact titers of monoclonal antibodies or polyclonal antibodies were calculated. Infection percentage was the percentage of cells in the positive region minus the uninfected cells in the positive region.

Infection control percentage=(1−infection percentage of sample cell/infection percentage of negative cell)×100%

Neutralization titer was defined as the highest dilution multiple by which the infection control percentage was just above 50%. Monoclonal and polyclonal antibodies were considered as having neutralizing capacity if their infection control percentage was above 50% after 50 times dilutions.

Measurement of Immune Protection of Animals Vaccinated with HPV6 VLPs

Female rabbits (general level), 6-8 weeks old, were purchased from the Disease Prevention and Control Center of Guangxi province, where they were raised. HPV6N3C-L1 VLPs prepared in Example 4, were mixed with equal amount of complete Freund's Adjuvant for the first immunization. For the booster, HPV6N3C-L1 VLPs were mixed with incomplete Freund's Adjuvant. Rabbits were immunized via muscle injection, with 100 μg per rabbit for the first immunization, and with 50 μg per rabbit for the booster separately at week 4, 10. After immunization, external vein blood was collected every week, and serum was separated and stored for detection.

Female goats (general level), 6-8 weeks old, were purchased from the Disease Prevention and Control Center of Guangxi province, where they were raised. HPV6N3C-L1 VLPs as prepared in Example 4, were mixed with equal amount of complete Freund's adjuvant for the first immunization. For the booster, HPV6N3C-L1 VLPs were mixed with incomplete Freund's adjuvant. Goats were immunized via muscle injection, with 1 mg per goat for the first immunization, and with 0.5 mg per goat for the booster separately at weeks 4, 10 and 18. After immunization, external vein blood was collected, and serum was separated and stored for detection.

Figure 5:
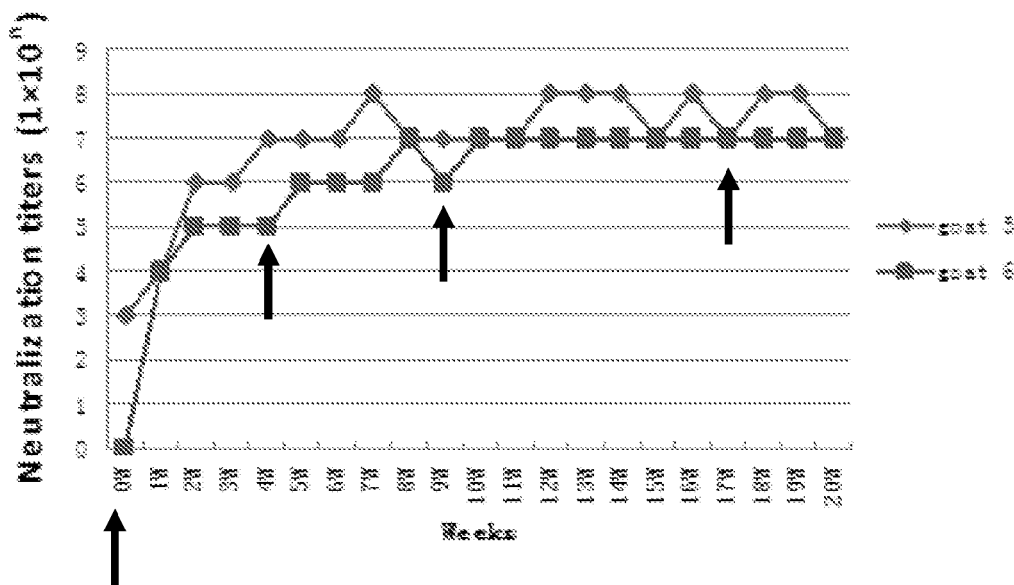
FIG. 5 shows titers of neutralizing antibodies in serum at different stages after vaccination of goat with HPV6N3C-L1 VLPs. Vaccination times are indicated with arrows. The titer of neutralizing antibodies increased rapidly a week after the first vaccination, and reached a peak level of $10^7$-$10^8$ after a booster.
Figure 6:
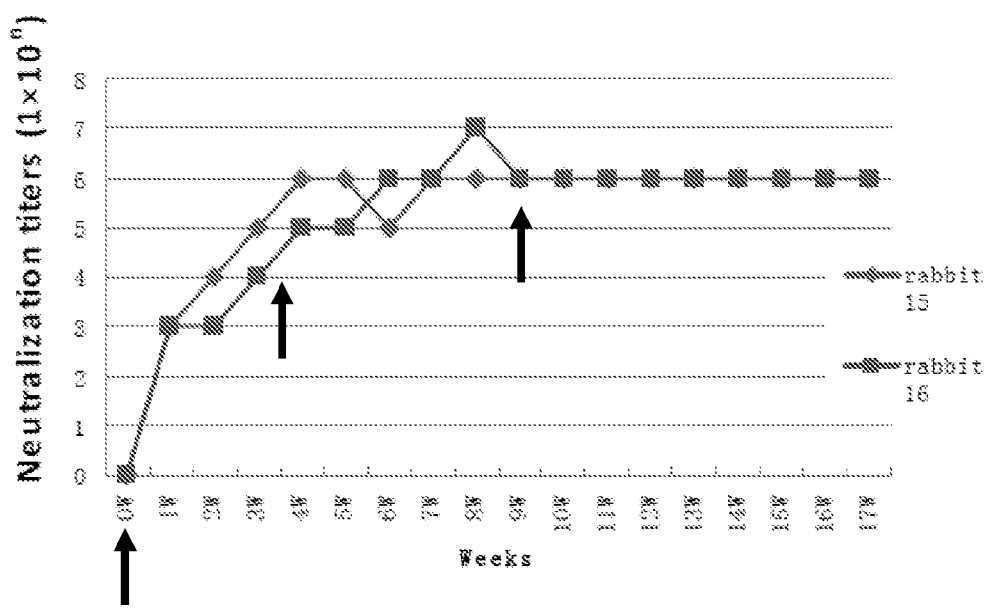
FIG. 6 shows titers of neutralizing antibodies in serum at different stages a week after vaccination of rabbit with HPV6N3C-L1 VLPs. Vaccination times are indicated with arrows. The titer of neutralizing antibodies increased rapidly a week after the first vaccination, and reached a peak level of $10^6$ after a booster.

Neutralization titers of the anti-serums were evaluated using a pseudovirion-based neutralization cell model assay. As shown in FIGS. 5 and 6, the vaccine produced by mixing HPV6N3C-L1 VLPs prepared in Example 4 with Freund's adjuvants (aluminum hydroxide or aluminum phosphate adjuvants available commercially or self-prepared may be used besides Freund's adjuvants) had good immunogenicity, could induce neutralizing antibodies with a high titer in animals, and could be used as an effective vaccine for the prevention of HPV infection.

Measurement of Immune Protection of Mice Vaccinated with HPV6/11 Bivalent Vaccine.

Four SPF BALB/c mice, 4-5 weeks old, were used. HPV6N5C-L1 and HPV11N4C-L1 VLPs, prepared according to the method similar to that of Examples 1-4, were mixed at a ratio of 1:2 (by weight), wherein the final concentrations of them were 40 μg/mL and 80 μg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 μg HPV6N5C-L1 and 20 μg HPV11N4C-L1 per mouse. The booster was administered every two weeks. The amount for the booster was 20 μg HPV6N5C-L1 and 40 μg HPV11N4C-L1 per mouse.

After immunization, external vein blood was collected every week and serum was separated. The titers of neutralizing antibodies against HPV6 and HPV11 in immunized mice were separately determined according to the method of Example 5.

Figure 7:
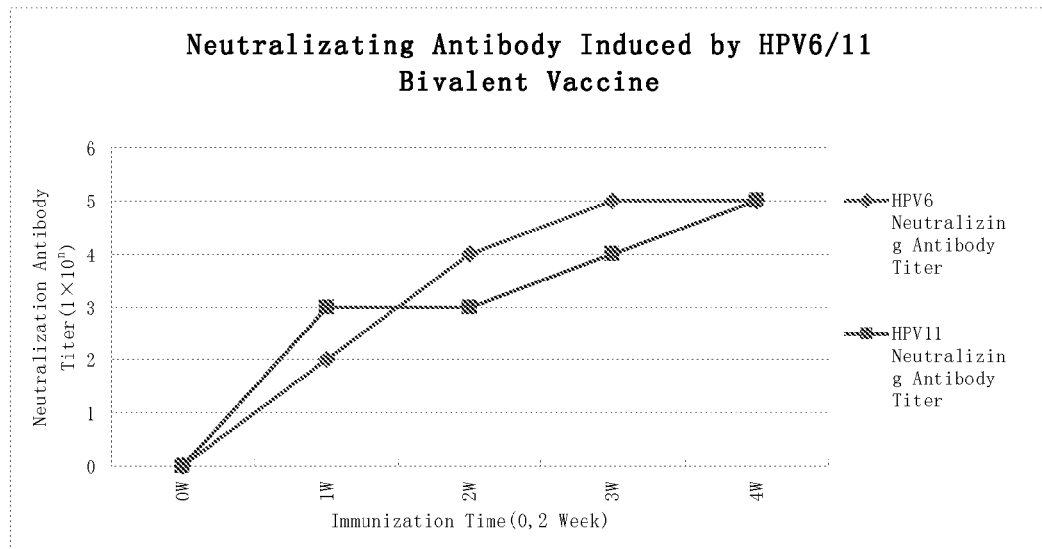
FIG. 7 shows the titers of neutralizing antibodies against HPV 6 and HPV11 in serum at different times after vaccination of mice with HPV6/11 bivalent vaccine obtained in Example 5. Vaccine was administered at 0 and 2 weeks. The titers of neutralizing antibodies against HPV6 and HPV 11 increased rapidly after the first vaccination, reaching $10^4$-$10^5$.

Results were shown in FIG. 7, indicating that HPV6/11 bivalent vaccine, prepared by blending HPV6N5C-L1 and HPV11N4C-L1 VLPs as prepared in Examples 1-4, had good immunogenicity, could induce neutralizing antibodies with a high titer against HPV 6 and HPV 11 in animals, and could be used as an effective vaccine for the prevention of HPV6/HPV11 infection (besides the Freund's adjuvants used in the experiments, the vaccine may be prepared by blending the two HPV6N5C-L1 and HPV11N4C-L1, with aluminum hydroxide or aluminum phosphate adjuvants available commercially or self-prepared).

The Amino Acid Sequence of HPV11N4C-L1 is showed in SEQ ID NO: 7 as follows.

```
Met Ser Asp Ser Thr Val Tyr Val Pro Pro Pro Asn Pro Val Ser Lys
1               5                   10                  15

Val Val Ala Thr Asp Ala Tyr Val Lys Arg Thr Asn Ile Phe Tyr His
                20                  25                  30

Ala Ser Ser Ser Arg Leu Leu Ala Val Gly His Pro Tyr Tyr Ser Ile
            35                  40                  45

Lys Lys Val Asn Lys Thr Val Val Pro Lys Val Ser Gly Tyr Gln Tyr
        50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190
```

-continued

```
Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys
```

Measurement of Immune Protection of Mice Vaccinated with HPV6/11/16/18 Quadrivalent Vaccine Four SPF BALB/c mice, 4-5 weeks old, were used. HPV6N5C-L1, HPV11N4C-L1, HPV16N30C-L1 and HPV18N65C-L1 VLPs, prepared according to the method similar to that of Examples 1-4, were mixed at a ratio of 1:2:2:1 (by weight), wherein the final concentrations of them were 40 µg/mL, 80 µg/mL, 80 µg/mL and 40 µg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 µg HPV6N5C-L1, 10 µg HPV18N65C-L1, 20 µg HPV11N4C-L1, and 20 µg HPV16N30C-L1 per mouse. The booster was administered every two weeks. The amount for the booster was 20 µg HPV6N5C-L1, 20 µg HPV18N65C-L1, 40 µg HPV11N4C-L1, and 40 µg HPV16N30C-L1 per mouse.

After immunization, external vein blood was collected every week and serum was separated. The titers of neutralizing antibodies against HPV6, HPV11, HPV16 and HPV18 in immunized mice were separately determined according to the method of Example 5.

Figure 8:
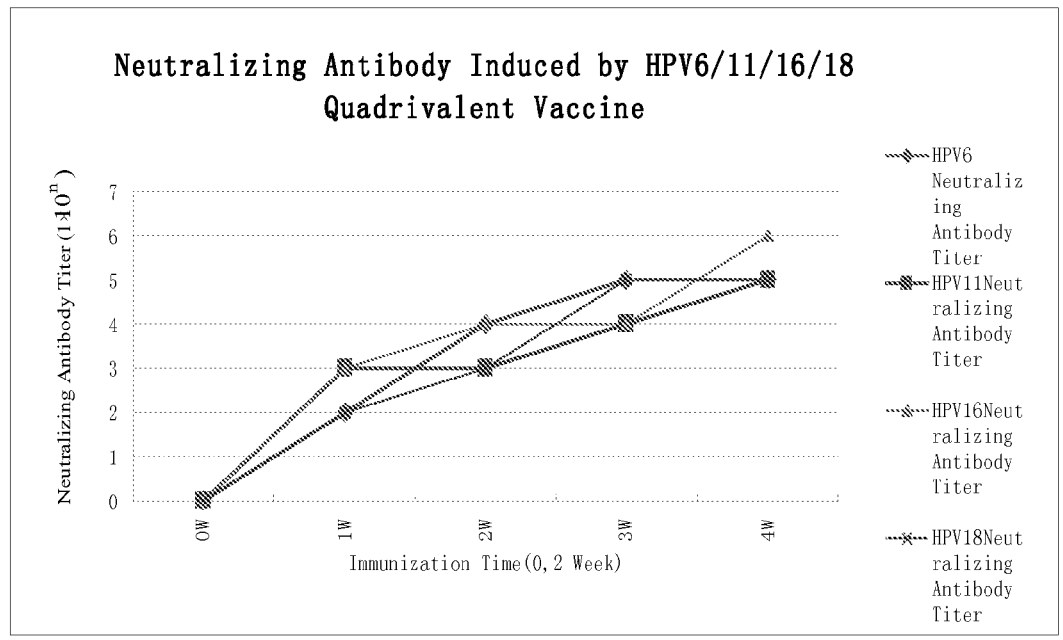
FIG. 8 shows the titers of neutralizing antibodies against HPV 6, HPV 11, HPV 16 and HPV 18 in serum at different times after vaccination of mice with HPV6/11/16/18 quadrivalent vaccine obtained in Example 5. Vaccine was administered at 0 and 2 weeks. The titers of neutralizing antibodies against HPV 6, HPV 11, HPV 16 and HPV 18 increased rapidly after the first vaccination, reaching $10^5$-$10^6$.

Results were shown in FIG. 8, indicating that HPV6/11/16/18 quadrivalent vaccine, prepared by blending HPV6N5C-L1, HPV11N4C-L1, HPV16N30C-L1 and HPV18N65C-L1 VLPs as prepared in Examples 1-4, had good immunogenicity, could induce neutralizing antibodies with a high titer against HPV 6, HPV 11, HPV 16, and HPV 18 in animals, and could be used as a effective vaccine for the prevention of HPV6/HPV11/HPV16/HPV18 infection (in addition to the Freund's adjuvants used in the experiments, the vaccine could be prepared by blending the four HPV6N5C-L1, HPV11N4C-L1, HPV16N30C-L1 and HPV18N65C-L1 VLPs with aluminum hydroxide or aluminum phosphate adjuvants available commercially or self-prepared).

The Amino Acid Sequence of L1 of HPV6N5C-L1 is showed in SEQ ID NO 4 as follows.

The Amino Acid Sequence of L1 of HPV16N30C-L1 is showed in SEQ ID NO 8 as follows.

```
Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
            245                 250                 255

Leu Phe Asn Arg Ala Gly Ala Val Gly Asp Asn Val Pro Asp Asp Leu
        260                 265                 270

Tyr Ile Lys Gly Ser Gly Ser Thr Ala Asn Leu Ala Ser Ser Asn Tyr
            275                 280                 285

Phe Pro Thr Pro Ser Gly Ser Met Val Thr Ser Asp Ala Gln Ile Phe
        290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
            325                 330                 335

Thr Asn Met Ser Leu Cys Ala Ala Ile Ser Thr Ser Glu Thr Thr Tyr
        340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400
```

-continued

```
Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
    450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
                500
```

The Amino Acid Sequence of L1 of HPV18N65C-L1 is showed in SEQ ID NO 9 as follows.

```
Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
        50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285
```

```
Ser Pro Ser Pro Ser Gly Ser Ile Val Thr Ser Asp Ser Gln Leu Phe
    290                 295                 300
Asn Lys Pro Tyr Trp Leu His Lys Ala Gln Gly His Asn Asn Gly Val
305                 310                 315                 320
Cys Trp His Asn Gln Leu Phe Val Thr Val Val Asp Thr Thr Arg Ser
                325                 330                 335
Thr Asn Leu Thr Ile Cys Ala Ser Thr Gln Ser Pro Val Pro Gly Gln
            340                 345                 350
Tyr Asp Ala Thr Lys Phe Lys Gln Tyr Ser Arg His Val Glu Glu Tyr
        355                 360                 365
Asp Leu Gln Phe Ile Phe Gln Leu Cys Thr Ile Thr Leu Thr Ala Asp
    370                 375                 380
Val Met Ser Tyr Ile His Ser Met Asn Ser Ser Ile Leu Glu Asp Trp
385                 390                 395                 400
Asn Phe Gly Val Pro Pro Pro Pro Thr Thr Ser Leu Val Asp Thr Tyr
                405                 410                 415
Arg Phe Val Gln Ser Val Ala Ile Ala Cys Gln Lys Asp Ala Ala Pro
            420                 425                 430
Ala Glu Asn Lys Asp Pro Tyr Asp Lys Leu Lys Phe Trp Asn Val Asp
        435                 440                 445
Leu Lys Glu Lys Phe Ser Leu Asp Leu Asp Gln Tyr Pro Leu Gly Arg
    450                 455                 460
Lys Phe Leu Val Gln Ala Gly Leu Arg Arg Lys Pro Thr Ile Gly Pro
465                 470                 475                 480
Arg Lys Arg Ser Ala Pro Ser Ala Thr Thr Ala Ser Lys Pro Ala Lys
                485                 490                 495
Arg Val Arg Val Arg Ala Arg Lys
            500
```

The Amino Acid Sequence of HPV11N4C-L1 VLP is shown in SEQ ID NO:7, as described above.

Example 6

Figure 9:
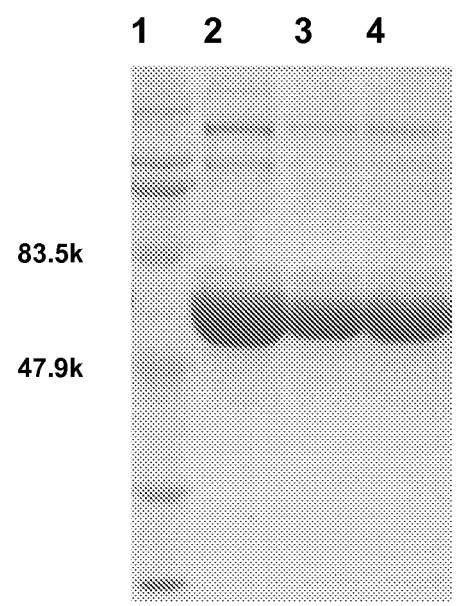
FIG. 9 shows the SDS-PAGE results of HPV6N2C-L1, HPV6N4C-L1 and HPV6N5C-L1 protein separately having 2, 4 and 5 amino acids truncated at the N-terminal of HPV 6 L1 protein (the amino acid sequences thereof set forth in SEQ ID Nos: 2, 3 and 4, respectively) during steps a)-e) of the method according to the invention. Lane 1: Molecular Weight Marker; Lane 2: HPV6N2C-L1 purified according to step a)-e), 10 μL; Lane 3: HPV6N4C-L1 purified according to step a)-e), 10 μL; Lane 4: HPV6N5C-L1 purified according to step a)-e), 10 μL. The result shows that the purity of HPV6N2C-L1, HPV6N4C-L1 and HPV6N5C-L1 protein separately having 2, 4 and 5 amino acids truncated at the N-terminal of HPV 6 L1 protein, reached about 98% following the steps a)-e).
Figure 11:
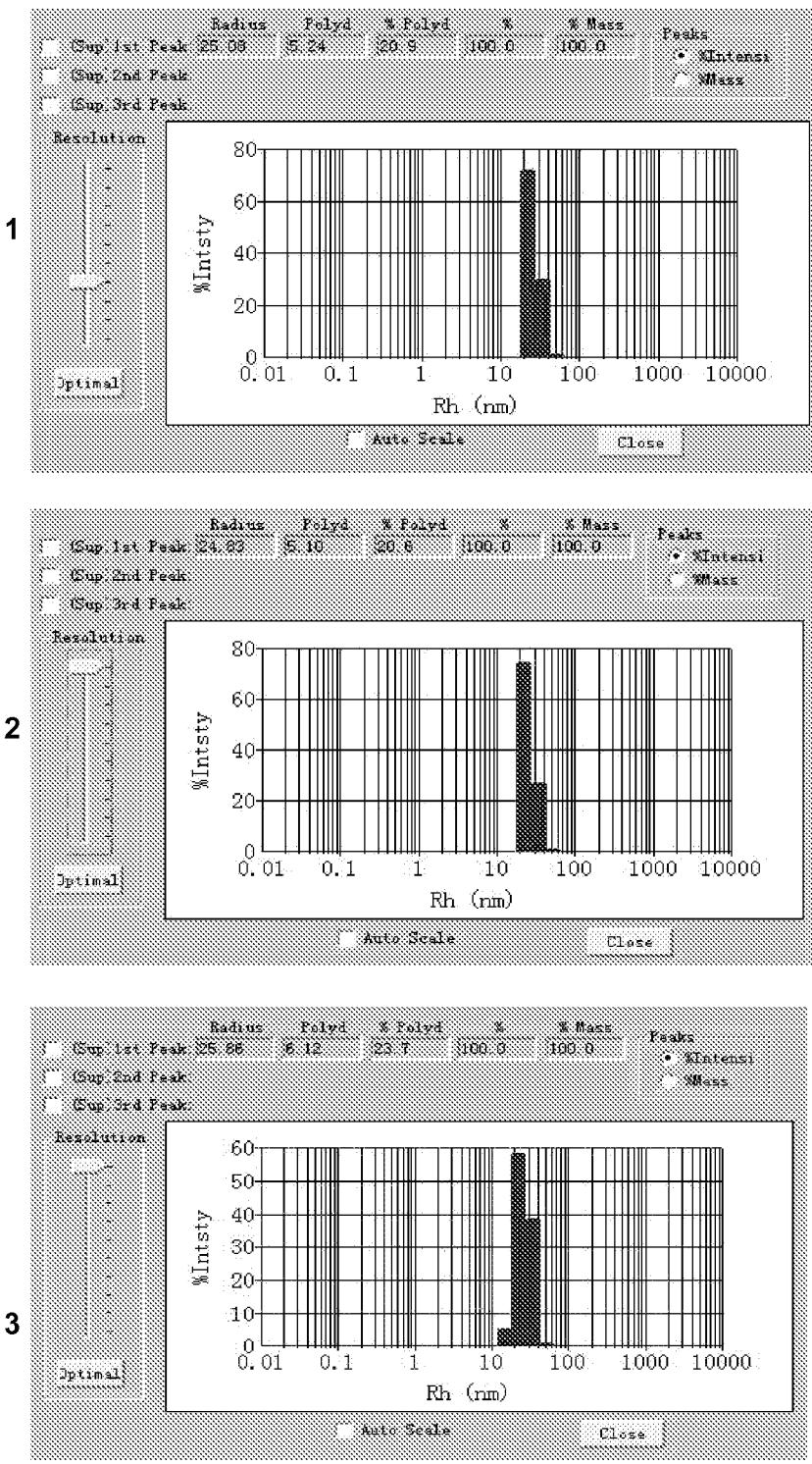
FIG. 11 shows the dynamic light-scattering measurement result of the VLPs of HPV6N2C-L1, HPV6N4C-L1 and HPV6N5C-L1 protein separately having 2, 4 and 5 acids truncated at the N-terminal of HPV 6 L1 protein obtained after steps a)-f). 1. The dynamic light-scattering measurement result of HPV6N2C-L1 VLPs obtained after steps a)-f). 2. The dynamic light-scattering measurement result of HPV6N4C-L1 VLPs obtained after steps a)-f). 3. The dynamic light-scattering measurement result of HPV6N5C-L1 VLPs obtained after steps a)-f). The result shows that HPV6N2C-L1 VLPs, HPV6N4C-L1 VLPs and HPV6N5C-L1 VLPs had a hydrodynamic radius of about 25 nm and a particle assembly rate of 100%.

The truncated HPV6L1 proteins set forth in SEQ ID NOs: 2, 3 and 4 were prepared according to the techniques used in examples 1-5. All these truncated proteins could be purified to an extent of above 98% and could be assembled into VLPs with a radius of about 25 nm. The results are shown in FIGS. 9, 10 and 11.

---

The invention claimed is:

1. A truncated recombinant human papillomavirus type 6 (HPV6) L1 protein consisting of an amino acid sequence selected from the group consisting of SEQ ID NOs: 1, 3 and 4.

2. A recombinant polynucleotide encoding the protein according to claim 1.

3. A recombinant vector comprising the polynucleotide according to claim 2.

4. An isolated cell comprising the recombinant vector according to claim 3.

5. A composition comprising the protein according to claim 1.

6. A human recombinant papillomavirus type 6 (HPV6) virus-like particle (VLP) comprising the protein according to claim 1.

7. An immunogenic composition comprising:
(1) human papillomavirus type 6 (HPV6) virus-like particles (VLP) comprising a truncated recombinant human papillomavirus type 6 (HPV6) L1 protein consisting of an amino acid sequence selected from the group consisting of SEQ ID NOs: 1 and 4,
(2) optionally, at least one HPV VLPs selected from the group consisting of VLPs of HPV type 11, 16, 18, 31, 33, 45, 52, and 58, and
(3) carriers or excipients.

8. An immunogenic composition comprising the recombinant protein of claim 1, and a carrier or excipient.

9. A method for inducing an immune response to HPV6 in an individual, comprising administering the composition according to claim 8 to an individual.

10. A method for inducing an immune response to HPV6 in an individual, comprising administering a composition comprising the HPV6 virus-like particle (VLP) according to claim 6 with carriers or excipients, and optionally, administering one or more VLPs selected from the group consisting of VLPs of HPV types 11, 16, 18, 31, 33, 45, 52, and 58.

11. A method for inducing an immune response to HPV6 in an individual, comprising administering the immunogenic composition according to claim 7 to an individual.

12. The immunogenic composition of claim 7, comprising human papillomavirus type 6 (HPV6) VLP and human papillomavirus type 11 (HPV11) virus-like particles (VLP), wherein the HPV6 VLP comprises the protein of SEQ ID NO:4, and wherein the HPV11 VLP comprises the protein of SEQ ID NO:7.

13. A method for inducing an immune response to HPV6 and HPV11 in an individual, comprising administering the immunogenic composition of claim 12 to an individual.

14. The immunogenic composition of claim 7, comprising human papillomavirus type 6 (HPV6) virus-like particle (VLP) comprising the protein of SEQ ID NO:4, a human papillomavirus type 11 (HPV11) VLP comprising the protein of SEQ ID NO:7, a human papillomavirus type 16 (HPV16) VLP comprising the protein of SEQ ID NO:8, and a human papillomavirus type 18 (HPV18) VLP comprising the protein of SEQ ID NO:9.

* * * * *